United States Patent
Majeti et al.

(10) Patent No.: US 12,371,469 B2
(45) Date of Patent: Jul. 29, 2025

(54) THERAPEUTIC ANTIGEN BINDING PROTEINS SPECIFIC FOR CD93 AND METHODS OF USE THEREOF

(71) Applicant: The Board of Trustees of the Leland Stanford Junior University, Stanford, CA (US)

(72) Inventors: Ravindra Majeti, Palo Alto, CA (US); Crystal Mackall, Stanford, CA (US); Jie Liu, Palo Alto, CA (US); Robbie Majzner, Palo Alto, CA (US); Rebecca Richards, Portola Valley, CA (US); Wan-Jen Hong, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1008 days.

(21) Appl. No.: 17/434,286

(22) PCT Filed: Feb. 28, 2020

(86) PCT No.: PCT/US2020/020449
§ 371 (c)(1),
(2) Date: Aug. 26, 2021

(87) PCT Pub. No.: WO2020/180706
PCT Pub. Date: Sep. 10, 2020

(65) Prior Publication Data
US 2022/0133794 A1     May 5, 2022

Related U.S. Application Data

(60) Provisional application No. 62/813,009, filed on Mar. 2, 2019.

(51) Int. Cl.
| | |
|---|---|
| C07K 16/00 | (2006.01) |
| A61K 40/11 | (2025.01) |
| A61K 40/31 | (2025.01) |
| A61K 40/42 | (2025.01) |
| A61P 35/00 | (2006.01) |
| C07K 14/725 | (2006.01) |
| C07K 16/28 | (2006.01) |
| C12N 5/0783 | (2010.01) |
| C12N 15/63 | (2006.01) |

(52) U.S. Cl.
CPC .......... *C07K 14/7051* (2013.01); *A61K 40/11* (2025.01); *A61K 40/31* (2025.01); *A61K 40/4202* (2025.01); *A61P 35/00* (2018.01); *C07K 16/2896* (2013.01); *C12N 5/0636* (2013.01); *C12N 15/63* (2013.01); *A61K 2239/31* (2023.05); *A61K 2239/38* (2023.05); *A61K 2239/48* (2023.05)

(58) Field of Classification Search
None
See application file for complete search history.

(56) References Cited

U.S. PATENT DOCUMENTS

| | | |
|---|---|---|
| 5,965,439 A | 10/1999 | Tenner et al. |
| 2012/0039911 A1 | 2/2012 | Park et al. |
| 2012/0093811 A1 | 4/2012 | Simmonds et al. |
| 2017/0151281 A1 | 6/2017 | Wagner et al. |
| 2017/0342148 A1 | 11/2017 | Heymann et al. |

FOREIGN PATENT DOCUMENTS

| | | | | |
|---|---|---|---|---|
| WO | WO2011016238 A1 | * | 2/2011 | ......... G01N 33/6896 |
| WO | WO2017189959 A1 | * | 11/2017 | ............. C12N 15/86 |
| WO | WO2018020222 | | 2/2018 | |
| WO | WO2018052789 | | 3/2018 | |

OTHER PUBLICATIONS

Chen C. et al. Enhancement and destruction of antibody function by somatic mutation: unequal occurrence is controlled by V gene combinatorial associations. EMBO J. Jun. 15, 1995;14(12):2784-94. (Year: 1995).*

Peptide [Internet]. Bethesda (MD): National Library of Medicine (US), National Center for Biotechnology Information; [1988]—. Accession No. MBB1710411, immunoglobulin heavy chain junction region, partial [*Homo sapiens*]; [2020]. (Year: 2020).*

Orlandini M. et al. The characterization of a novel monoclonal antibody against CD93 unveils a new antiangiogenic traget. Oncotarget. May 15, 2014;5(9):2750-60). (Year: 2014).*

Orlandini et al. (2014) "The characterization of a novel monoclonal antibody against CD93 unveils a new antiangiogenic target". Oncotarget. May 15, 2014, vol. 5, No. 9; pp. 2750-2760.

Miliotou et al. (2018) CAR T-cell Therapy: A New Era in Cancer Immunotherapy., Current Pharmaceutical Biotechnology, vol. 19, No. 1, pp. 5-18.

\* cited by examiner

*Primary Examiner* — Janet L Epps -Smith
*Assistant Examiner* — Estella M. Gustilo
(74) *Attorney, Agent, or Firm* — Pamela J. Sherwood; Bozicevic, Field & Francis LLP

(57) ABSTRACT

Antigen binding domain polypeptides (ABD) specific for human CD93 are provided, which ABD may be formatted as antibodies, as chimeric antigen receptors, and the like. T cells comprising an anti-CD93 CAR are useful in the treatment of cancer, e.g. hematologic malignancies.

20 Claims, 20 Drawing Sheets
Specification includes a Sequence Listing.

```
                              CDR1                    CDR2
EVQLQQSGPELVKPGASVKIPCKASGYTFT DYHMD WVKQSHGKSLEWIG DIDPYNGDT

CDR3
VFNQKFKG KATLTVDKSSSTAYMELRSLTSEDTAVYYC TRGGDY WGQGTTLTVSS
```

FIG. 1A

```
                              CDR1                        CDR2
DVVMTQTPLSLPVSLGDQASISC RSSQTLVHSNGNTYLH WYLQKPGQSPKLLIY KVSN

CDR3
RFS GVPDRFSGSGSGTDFTLKISRVEAEDLGVYFC SQSTHVPFT FGSGTKLEIK
```

FIG. 1B

```
                                              CDR1
F11VH     EVQLQQSGPELVKPGASVKIPCKASGYTFTDYHMDWVKQSHGKS
HuF11-VH  QVQLVQSGAEVKKPGASVKVSCKASGYTFTDYHMDWVKQAPGQG

CDR2
F11VH     LEWIGDIDPYNGDTVFNQKFKGKATLTVDKSSSTAYMELRSLTS
HuF11-VH  LEWIGDIDPYNGDTVFNQKFKGKATMTRDTSISTAYMELSRLRS

CDR3
F11VH     EDTAVYYCTRGGDYWGQGTTLTVSS
HuF11-VH  DDTAVYYCTRGGDYWGQGTLVTVSS
```

FIG. 2A

```
                                               CDR1
F11VL     DVVMTQTPLSLPVSLGDQASISCRSSQTLVHSNGNTYLHWYLQK
HuF11-VL  DIVMTQTPLSLSVTPGQPASISCRSSQTLVHSNGNTYLHWYLQK

CDR2
F11VL     PGQSPKLLIYKVSNRFSGVPDRFSGSGSGTDFTLKISRVEAEDL
HuF11-VL  PGQPPQLLIYKVSNRFSGVPDRFSGSGSGTDFTLKISRVEAEDV

CDR3
F11VL     GVYFCSQSTHVPFTFGSGTKLEIK
HuF11-VL  GVYFCSQSTHVPFTFGQGTKLEIK
```

FIG. 2B

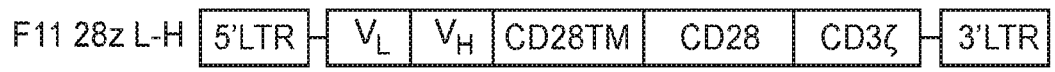
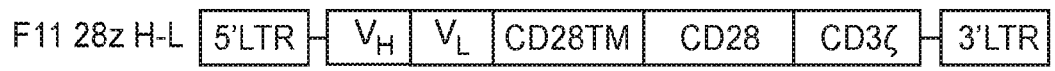
FIG. 7A
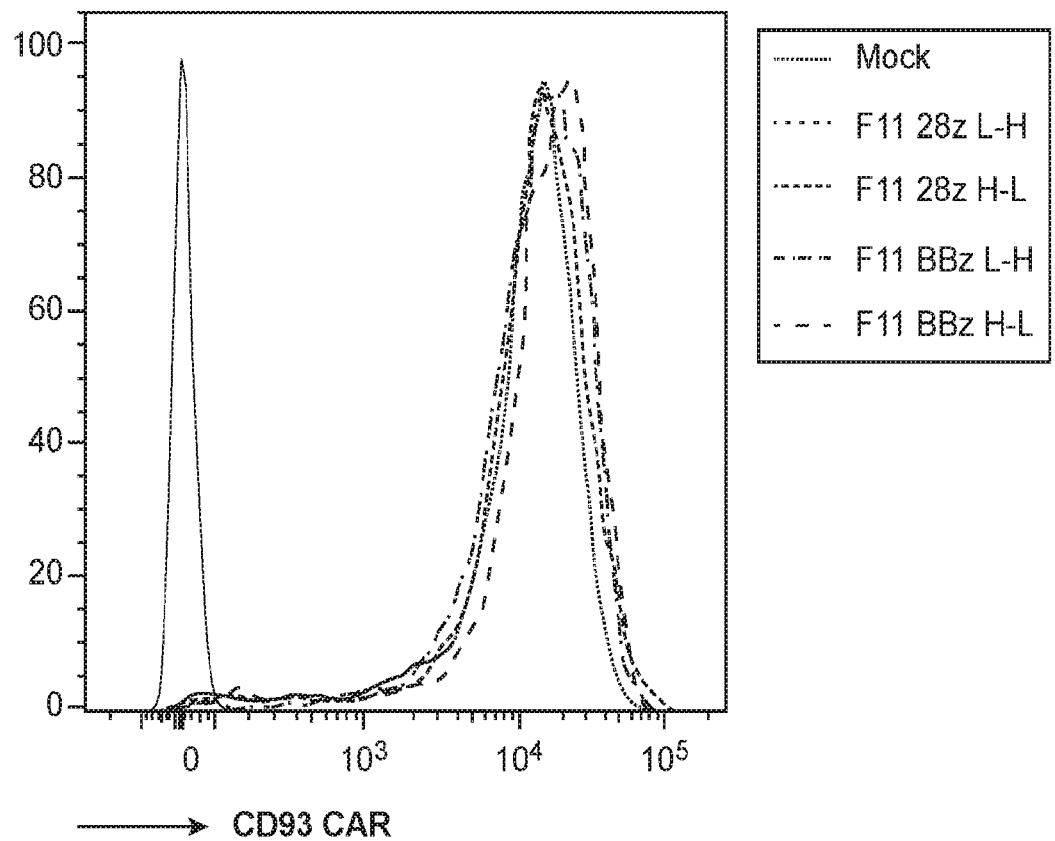
FIG. 7B

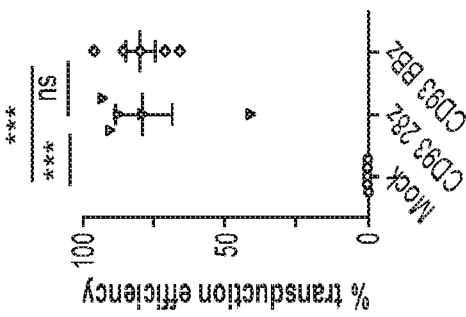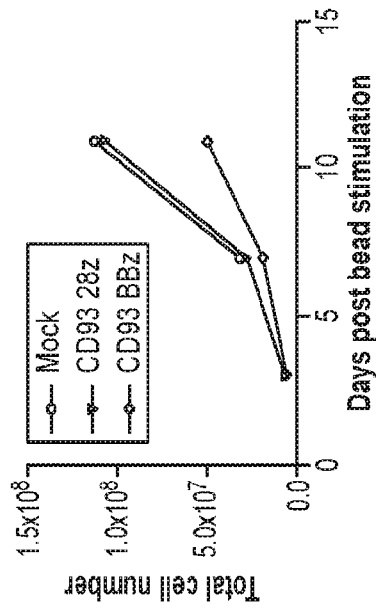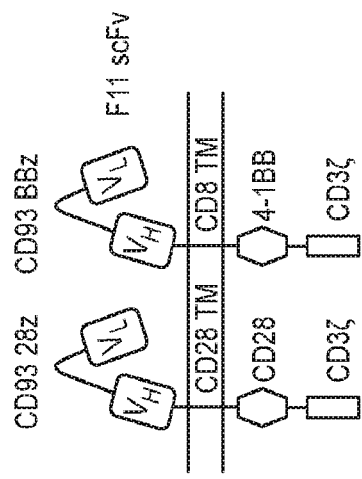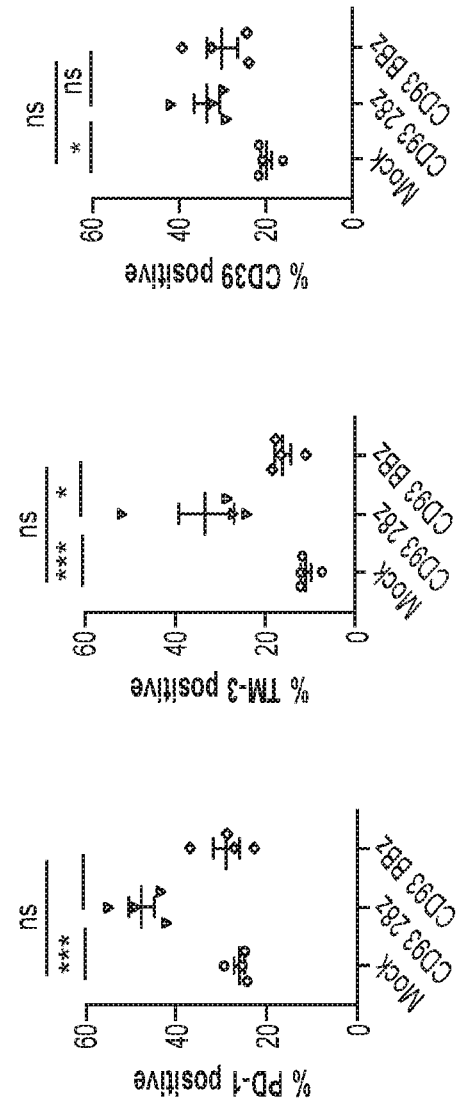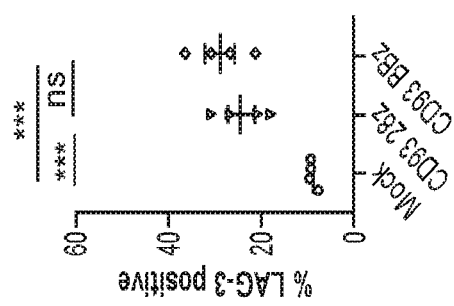
FIG. 12A
FIG. 12B
FIG. 12C
FIG. 12D

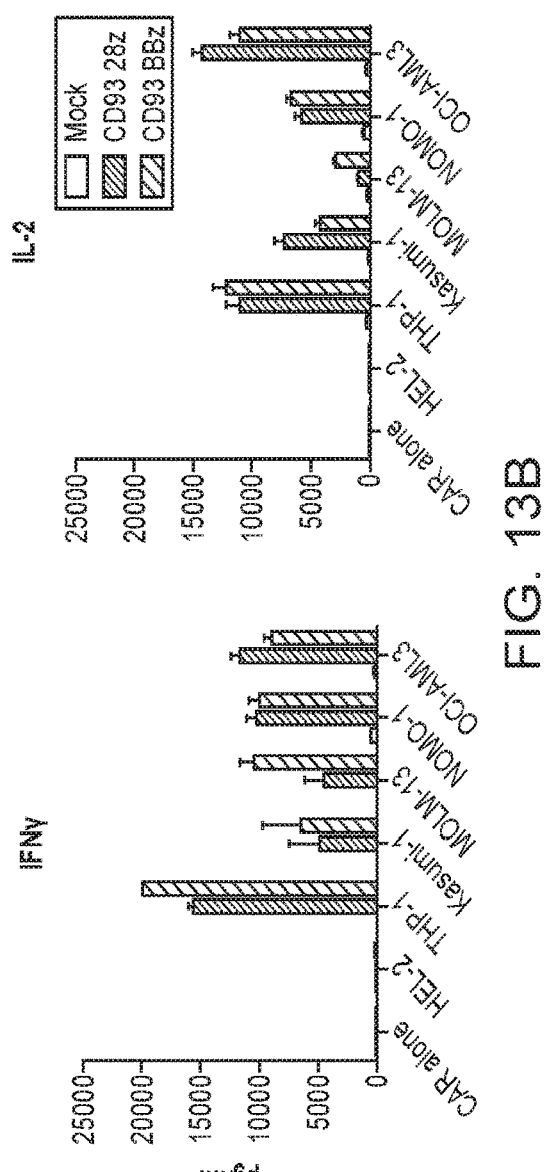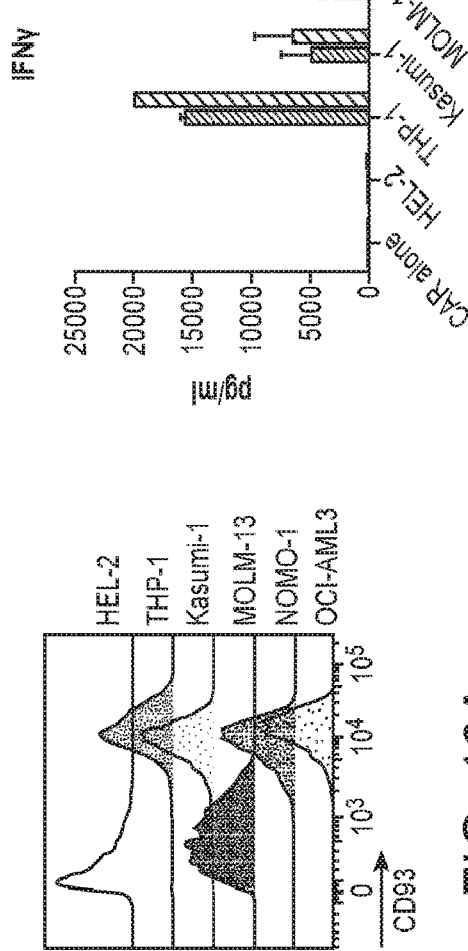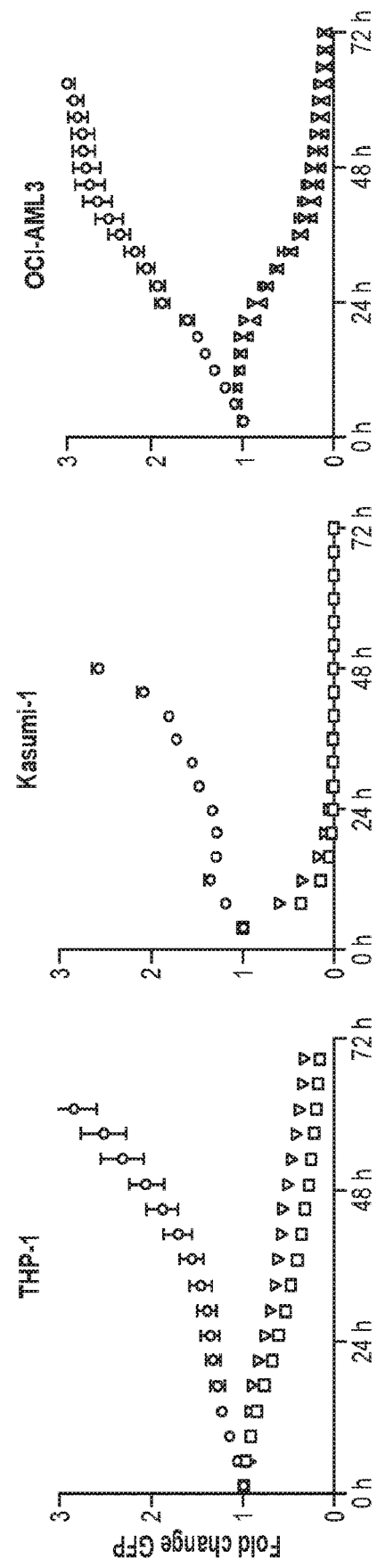
FIG. 13A
FIG. 13B
FIG. 13C

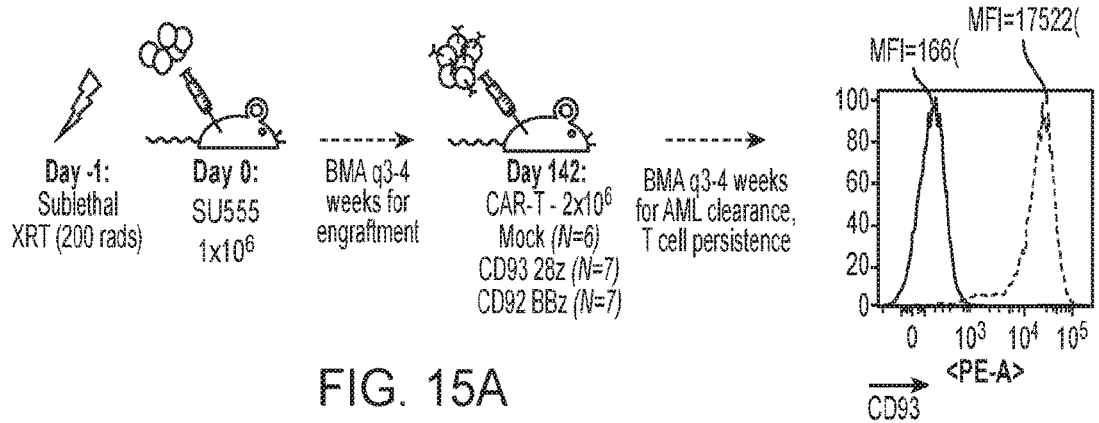
FIG. 15A
FIG. 15B
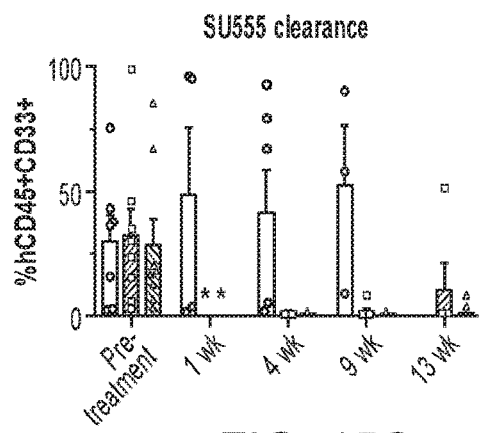
FIG. 15C
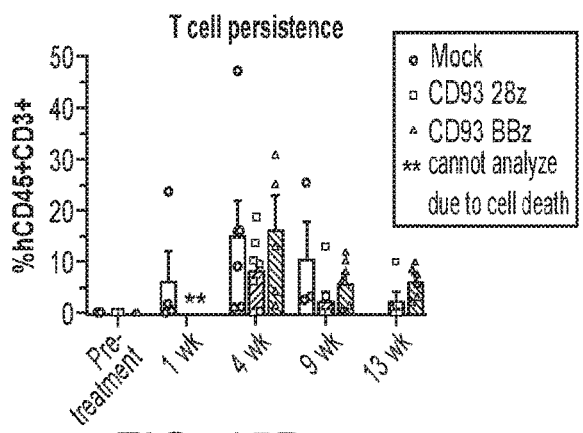
FIG. 15D
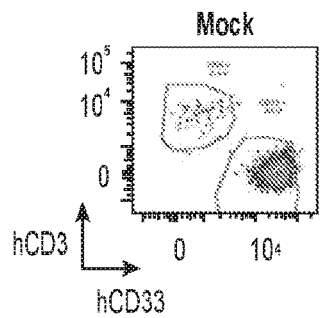
FIG. 15E
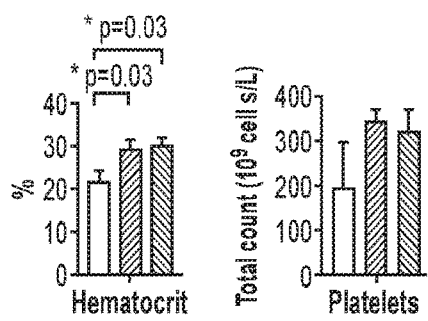
FIG. 15F
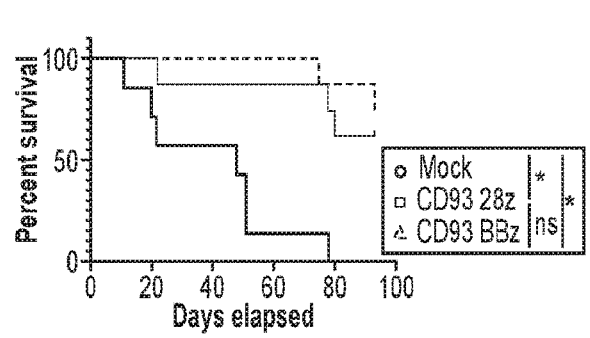
FIG. 15G

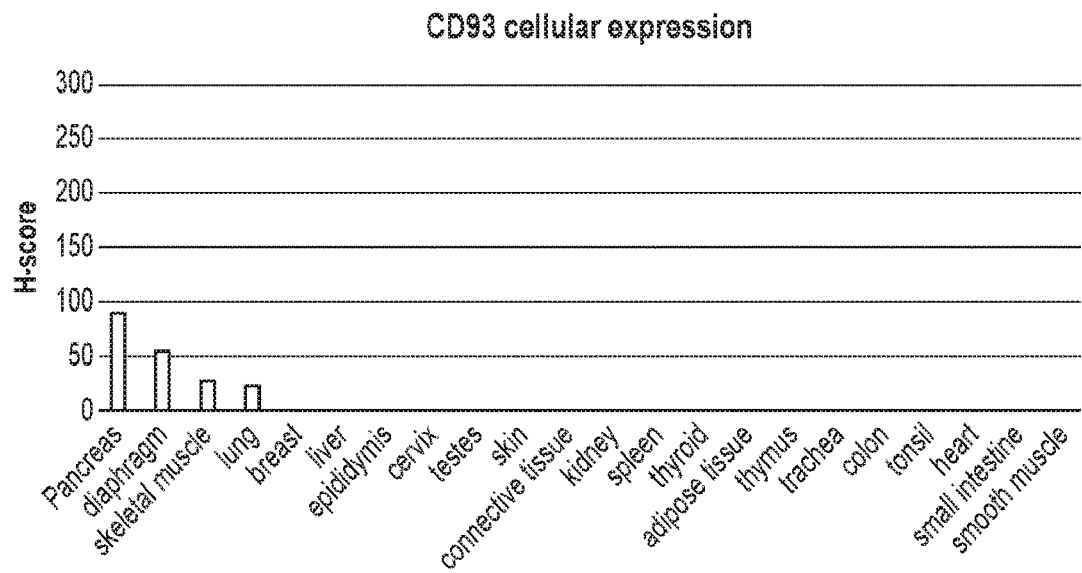
FIG. 17B
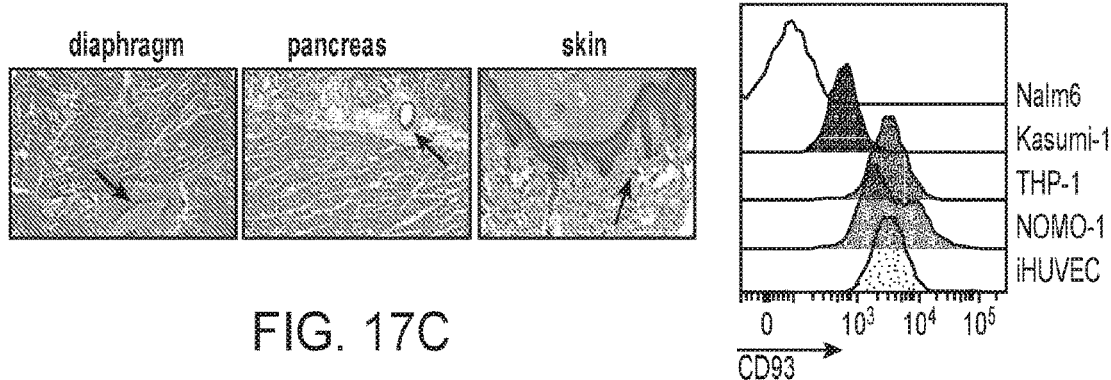
FIG. 17C
FIG. 17D
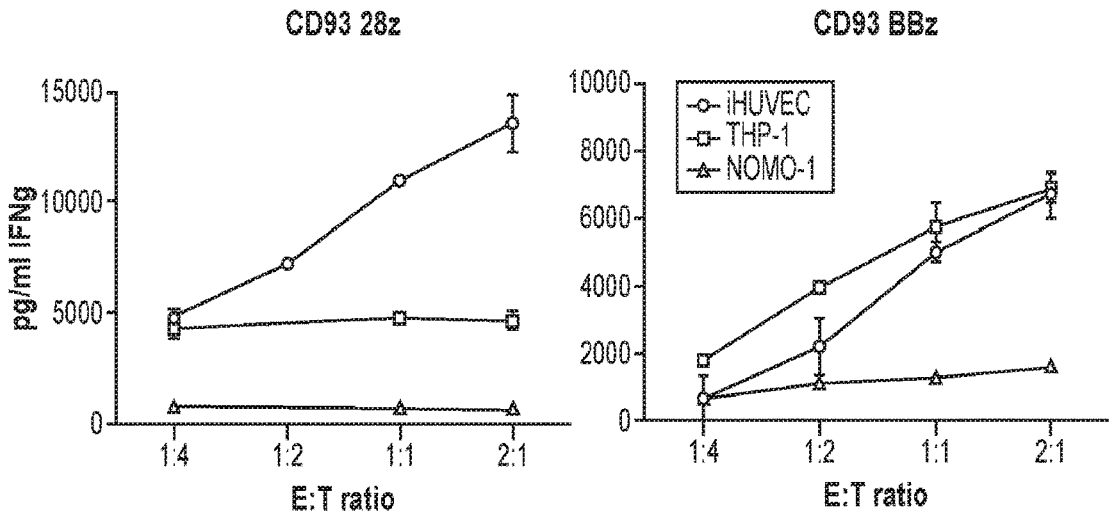
FIG. 17E

THERAPEUTIC ANTIGEN BINDING PROTEINS SPECIFIC FOR CD93 AND METHODS OF USE THEREOF

CROSS REFERENCE

This application claims benefit of U.S. Provisional Patent Application No. 62/813,009, filed Mar. 2, 2019, which applications are incorporated herein by reference in their entirety.

BACKGROUND

Immuno-oncology has emerged in recent years as a potent approach to the treatment of cancer, by leveraging the capabilities of an individual's immune system to eliminate cancer cells. In the course of cancer progression there can be a series of adaptive responses by cancer cells to evade host immune responses, in which cancer cells evade cytotoxic or proinflammatory immune responses by altering their phenotype. This adaptive process may be triggered by specific or non-specific immune mechanisms. Cancer cells may, for example, hijack mechanisms that normally limit inflammatory and immune responses, and thereby protect themselves. In various aspects, immunotherapy can block these cancer evasion mechanisms and restore immune responses against cancer cells. Immunotherapy thus has the potential to make cancer cells visible to the immune system again, triggering active or passive immunity-mediated control of cancer.

A variety of therapies are in clinical use, or are in clinical trials, for enhancing host immune system responses to cancer, including for example: checkpoint blockade to revitalize exhausted T cells no longer responsive to tumor antigens; blockade of innate immune cell mechanisms that prevent phagocytic cells from destroying cancer cells; administration of cytokines, such as IL-2, that enhance T cell activity; administration of antibodies that selectively bind to tumor cell antigens and enhance killing by antibody dependent mechanisms, such as antibody dependent cellular cytotoxicity (ADCC); expansion and activation in vitro of host T cells or host dendritic cells; and the like.

The effectiveness of T cell based therapies can vary with the antigenic selectivity of the T cells that are administered or activated. Antigenic specificity can be altered by genetic modification and redirection of T-cells to target antigens that are overexpressed in tumors. One approach for modification has been to engineer patient T-cells to express chimeric antigen receptors (CARs), in order to generate T-cells more efficient at targeting tumors. T-cells have been used for this purpose by first modifying the cells by viral and non-viral transfection methods and then expanding the modified cells in culture for reintroduction into the patient.

The extracellular domain of a CAR comprises an antigen binding domain, usually separated by a spacer from the transmembrane domain. Single chain variable regions derived from antibodies have been frequently used for this purpose, although antigen binding domains such as Fab fragments, and other ligands have also been used. The use of these antigen binding domains allows CARs to bypass MHC restriction for antigen recognition.

CAR T cells have been successfully used in the treatment of hematologic malignancies, for example with anti-CD19 CAR T cells being used to treat B-cell non-Hodgkin lymphoma (NHL), acute lymphoblastic leukemia (ALL), multiple myeloma (MM), and chronic lymphocytic leukemia (CLL). Other antigens for treatment of hematologic malignancies have included CD20, and CD30.

Despite the remarkable high response rate of CAR T-cells in lymphocytic leukemias, however, antigen escape has been observed in a number of patients. Thus, there is the need for discovery of novel targeting hematologic markers and development of targeted therapies for safer and more efficient approaches.

SUMMARY

Compositions and methods are provided relating to CD93 antigen binding domains (ABD). The anti-CD93 ABD are comprised of one or more variable region polypeptides that specifically bind to human CD93. The ABD may be linked, e.g. conjugated or fused, to various effector polypeptides, which include without limitation chimeric antigen receptors; antibodies; and fragments and derivatives thereof, which polypeptides may be referred to as an anti-CD93 ABD construct. Embodiments include polynucleotides encoding the ABD; vectors comprising polynucleotides encoding the anti-CD93 ABD; cells engineered to express the anti-CD93 ABD; and pharmaceutical formulations comprising cells engineered to express the anti-CD93 ABD. The anti-CD93 ABD find particular utility as reagents for the diagnosis and immunotherapy of disease associated with CD93 in humans, particularly in cancer therapy.

In an embodiment, the anti-CD93 ABD is covalently linked, e.g. conjugated or fused, to an effector polypeptide of a CAR. In some embodiments, the anti-CD93 ABD of a CAR is a single chain variable region. In some embodiments the anti-CD93 ABD comprises humanized variable region sequences. In some embodiments an anti-CD93 CAR is expressed by a human T cell. In some embodiments an anti-CD93 CAR is a bi-specific CAR, where a second antigenic specificity may be an antigen present on malignant hematologic cells, e.g. CD123, FLT3, TIM3, CD99, CD96, B7-H3, CD33, IL1RAP, CLL1 (CLEC12A), etc. In other embodiments an engineered T cell expresses an anti-CD93 CAR and a second CAR with specificity for an antigen present on malignant hematologic cells.

In some embodiments a T cell is genetically modified to introduce a genetic sequence encoding an anti-CD93 CAR in an ex vivo procedure, prior to transfer into a subject. In some embodiments, the genetically modified cells are expanded in vitro. An effective dose of the genetically modified cells can be administered to a patient in need thereof. T cells include without limitation, naïve CD8+ T cells, cytotoxic CD8+ T cells, naïve CD4+ T cells, helper T cells, e.g., TH1, TH2, TH9, TH11, TH22, TFH; memory T cells, e.g., central memory T cells, stem cell memory T cells (TSCM), effector memory T cells, NK T cells, etc. In some embodiments, engineered T cells comprise a complex mixture of immune cells, e.g., tumor infiltrating lymphocytes (TILs) isolated from an individual in need of treatment.

In other embodiments the anti-CD93 ABD is provided as a polypeptide linked, e.g. conjugated or fused, to an immunoglobulin effector sequence, for example as an scFv, as a full length chimeric or humanized antibody, e.g. having a human immunoglobulin constant region of any isotype, e.g. IgG1, IgG2, IgG3, IgG4, IgA, etc., or an antibody fragment, e.g. a F(ab')$_2$ fragment, and F(ab) fragment, etc. An anti-CD93 antibody may be labeled with a detectable label, immobilized on a solid phase and/or conjugated with a heterologous compound. The antibody may also be provided as a bi-specific or multispecific antibody reactive with a second antigen, particularly including other cancer antigens; or with immunotherapy reagents, e.g. anti-CD3, anti-PD-1/PD-L1, anti-CTLA-4, anti-CD40, anti-CD47, and the like.

Embodiments include anti-CD93 CARs, anti-CD93 antibodies and derivatives and fragments thereof that comprise an anti-CD93 ABD having one or both of a variable heavy (VH) and a variable light (VL) domain polypeptide, where a VH polypeptide comprises least one, at least two, up to 3 VH CDR sequences as provided herein and as set forth in SEQ ID NO:3, 4 and 5, and a VL polypeptide comprises least one, at least two, up to 3 VL CDR sequences as provided herein and as set forth in SEQ ID NO: 8, 9 and 10, in combination with framework sequences from a variable region, e.g. human VH or VL framework sequences. In some embodiments an anti-CD93 ABD comprises at least one VL sequence comprising the 3 light chain CDR sequences provided herein situated in a variable region framework, which may be, without limitation, a human or mouse variable region framework, and at least one VH sequence comprising the 3 heavy chain CDR sequence provided herein situated in a variable region framework, which may be, without limitation, a human or mouse variable region framework.

In some embodiments, the anti-CD93 ABD comprises an amino acid sequence variant of one or more of the CDRs of the provided VH and VL sequences, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally have a binding affinity for human CD93 of at least about $10^{-8}$ M and will bind to the same epitope as an anti-CD93 ABD having the amino acid sequence of those set forth herein.

In some embodiments, a therapeutic method is provided, particularly relating to the elimination of cancer cells expressing CD93, including without limitation hematologic malignant cells. In some embodiments the cancer is a hematologic malignancy, where the cancer cells express CD93. In some embodiments the hematologic malignancy is a leukemia, including without limitation acute myelogenous leukemia (AML) and mixed lineage leukemia (MLL). In some embodiments the hematologic malignancy is a myelodysplastic syndrome (MDS) disorder. In some embodiments the hematologic malignancy is a myeloproliferative neoplasm (MPN), which disorders include, without limitations myelofibrosis, essential thrombocythemia, polycythemia vera, etc. A method can comprise introducing into a recipient in need, e.g. an individual with cancer, an engineered cell population, wherein the cell population has been modified by introduction of a sequence encoding an anti-CD93 ABD, particularly an anti-CD93 CAR, in a dose effective to reduce the number of cancer cells present in the recipient. The cell population may be engineered ex vivo, and is usually autologous or allogeneic with respect to the recipient.

In some embodiments, an engineered cell is provided, e.g. an engineered T cell, in which the cell has been modified by introduction of an anti-CD93 ABD coding sequence, e.g. an anti-CD93 CAR, an anti-CD93 scFv, an anti-CD93 antibody, etc. The engineered cell can be provided in a unit dose for therapy, and can be allogeneic, autologous, etc., with respect to an intended recipient. Introduction of the coding sequence can be performed in vivo or in vitro, using any appropriate vector, e.g., viral vectors, integrating vectors, and the like.

In some embodiments, a vector comprising a polynucleotide sequence encoding a polypeptide comprising an anti-CD93 ABD provided, where the coding sequence is operably linked to a promoter active in the desired cell. In some embodiments, the promoter may be constitutive or inducible. Various vectors are known in the art and can be used for this purpose, e.g. viral vectors, plasmid vectors, minicircle vectors, which vectors can be integrated into the target cell genome, or can be episomally maintained. The vector may be provided in a kit.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1. Amino acid sequence of variable heavy (A) and light (B) regions. CDRs are underlined.

FIG. 2. Comparison of mouse and humanized F11 variable heavy (A) and light (B) regions. CDRs are marked as indicated.

FIG. 7. CD93 CAR T cell constructs and expression in primary human T cells. A. Four variations of CD93-specific CAR T cells were generated, with varying order of the $V_L$ and $V_H$ portions of the scFv, with either CD28 or 41-BB intracellular co-stimulation domains (and CD28 or CD8 transmembrane domains, respectively) followed by CD3ζ. Each construct was inserted into the MSGV1 retroviral vector. B. Primary human T cells transduced with each of the four retroviruses derived from the CD93 F11 constructs were stained with CD93-Fc fusion protein followed by anti-human IgG Fc. All retroviral constructs had high transduction efficiency and similar CAR expression levels.

FIG. 12. CAR design, expansion, and expression. (A) CD93 CAR constructs were designed using the scFv of the humanized mCD93 antibody (F11), and cloned into retroviral plasmids. (B) Expansion kinetics of CD93 CAR T cells after retroviral transduction of primary T cells. Both CAR T cell products expand robustly, though CD93 BBz expands with slower kinetics than CD93 28z. (C) Transduction efficiency on day 10 post-activation is consistently above 70% for CD93 CAR T cells. (D) Markers that represent exhausted T cells are elevated in CD93 28z compared to CD93 BBz.

FIG. 13. Cytokine production and cytotoxicity of CD93 CAR T cells against AML cell lines. (A) AML cell lines were stained with humanized anti-CD93 antibody. (B) CD93 CAR T cells harvested 10 days after activation were incubated without tumor cells or AML cells and cytokines were measured by ELISA. (C) CD93 CAR T cells harvested 10 days after activation were co-incubated with THP-1, Kasumi-1, or OCI-AML3 cells at a 1:1 E:T ratio; cytotoxicity was measured by Incucyte assay. Both CD93 28z and CD93 BBz CAR T cells exhibited specific and robust cytotoxicity.

FIG. 15. CD93 CAR T cell efficacy and persistence in a patient derived xenograft model. (A) Experimental design: $1 \times 10^6$ SU555 AML cells were injected into sub-lethally irradiated NSG, and serial bone marrow aspirates (BMA) showed adequate levels of engraftment 4 months later. Mice were randomized and treated with $2 \times 10^6$ mock transduced (N=6), CD93 28z (N=7) or CD93 BBz (N=7) CAR T cells, then followed with serial BMA for clearance of leukemia and persistence of T cells. (B) CD93 expression on SU555 measured with F11 antibody. (C) Leukemia engraftment (% CD45+CD33+) and (D) CAR T cell persistence (% CD45+CD3+) were measured by flow cytometry from BMA for up to 13 weeks after treatment (E) Flow cytometry of BMA 1 week after treatment with mock T cells or CD93 CAR T cells. There were no measurable live cells within the BM of the CAR-treated animals. (F) CBC done at 2 weeks after treatment reveals cytopenias in the mock-treated group and normal hematocrit and platelets in the recovering bone marrow of the CD93 CAR-treated animals. (G) CD93 CAR T cells confer a significant survival based on Gehan-Breslow-Wilcoxson test.

DETAILED DESCRIPTION OF THE EMBODIMENTS

Figure 3:
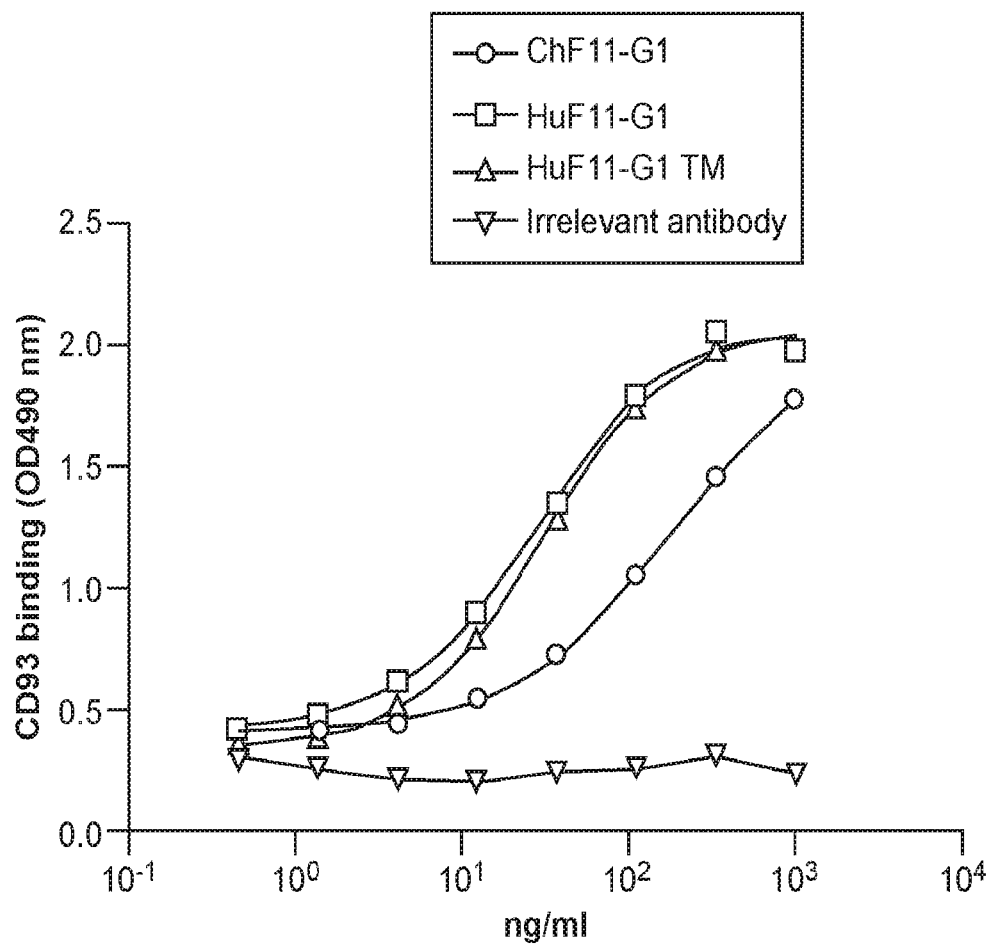
FIG. 3. Humanized and chimeric F11 monoclonal antibodies bind human CD93 with similar affinity. Human CD93/Fc fusion protein was coated in a 96-well plate and different concentrations of the antibodies as indicated were added. HRP-conjugated anti-human kappa antibody was used as a secondary antibody. CD93 binding activity was measured by reading signals at $OD_{490}$ nm.

In order for the present disclosure to be more readily understood, certain terms and phrases are defined below as well as throughout the specification. The definitions provided herein are non-limiting and should be read in view of what one of skill in the art would know at the time of invention.

Definitions

Before the present methods and compositions are described, it is to be understood that this invention is not limited to the particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential methods and materials are now described. All publications mentioned herein are incorporated herein by reference to disclose and describe the methods and/or materials in connection with which the publications are cited.

As used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Further, the dates of publication provided may be different from the actual publication dates which may need to be independently confirmed.

CD93. CD93 is a C-type lectin transmembrane receptor that plays a role in cell-cell adhesion and in defense mechanisms. It comprises a C-type lectin domain, a series of epidermal growth factor like domains, a highly glycosylated mucin-like domain, a unique transmembrane domain and a short cytoplasmic tail. It is reported to be involved in clearance of apoptotic cells. The CD93 sequence share identity with thrombomodulin. The reference sequence of the human CD93 protein may be accessed at Genbank NP_036204; and the genetic sequence at NM_012072.

Figure 4:
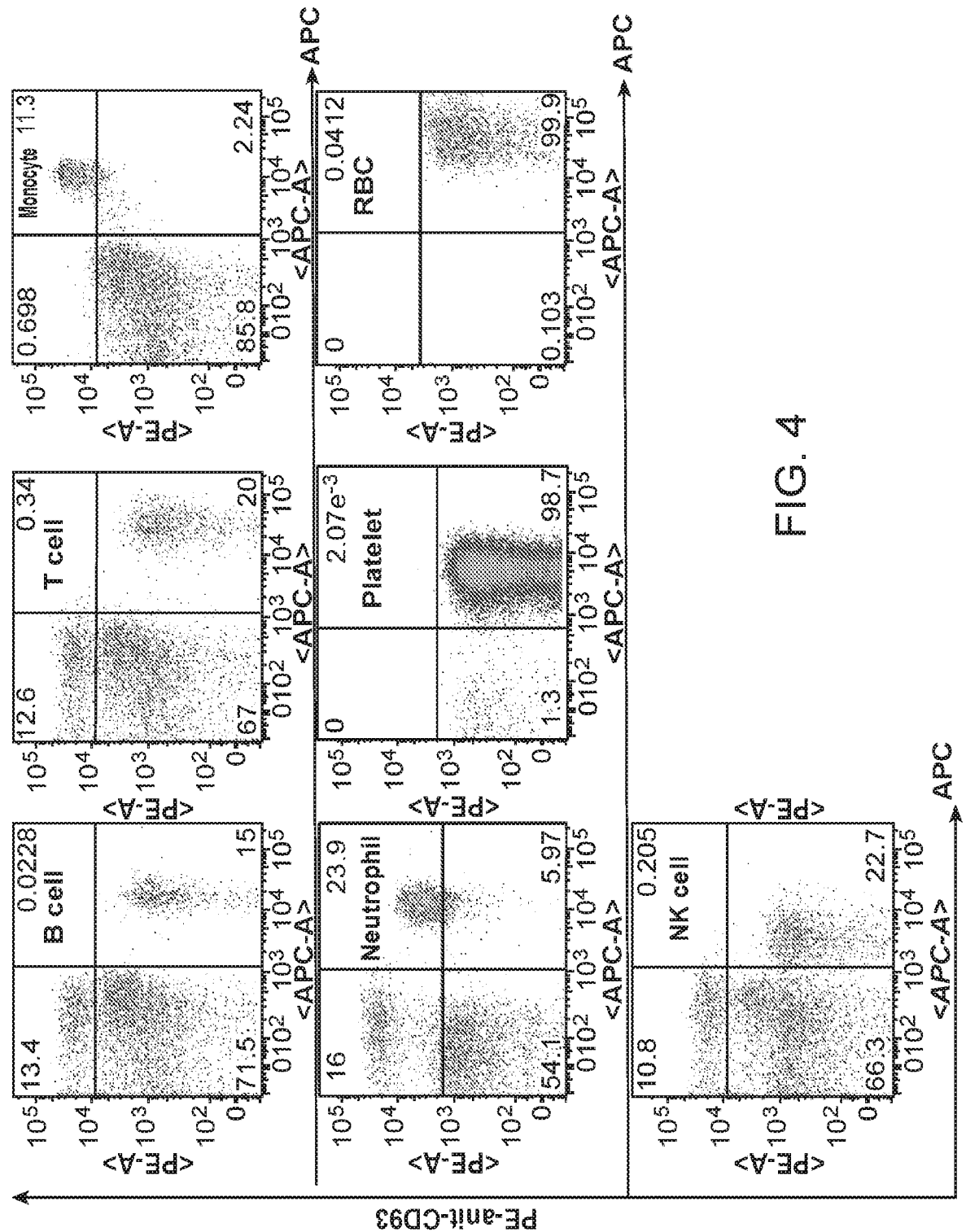
FIG. 4. CD93 expression on normal human leukocytes. Human peripheral blood was co-stained with PE-conjugated anti-CD93 antibody and APC-conjugated anti-CD19, CD3, CD14, CD15, CD41a, CD235a, or CD56 for B cells, T cells, monocytes, neutrophils, platelets, red blood cells, and NK cells, respectively. Data represent one out of three donors.
Figure 5A:
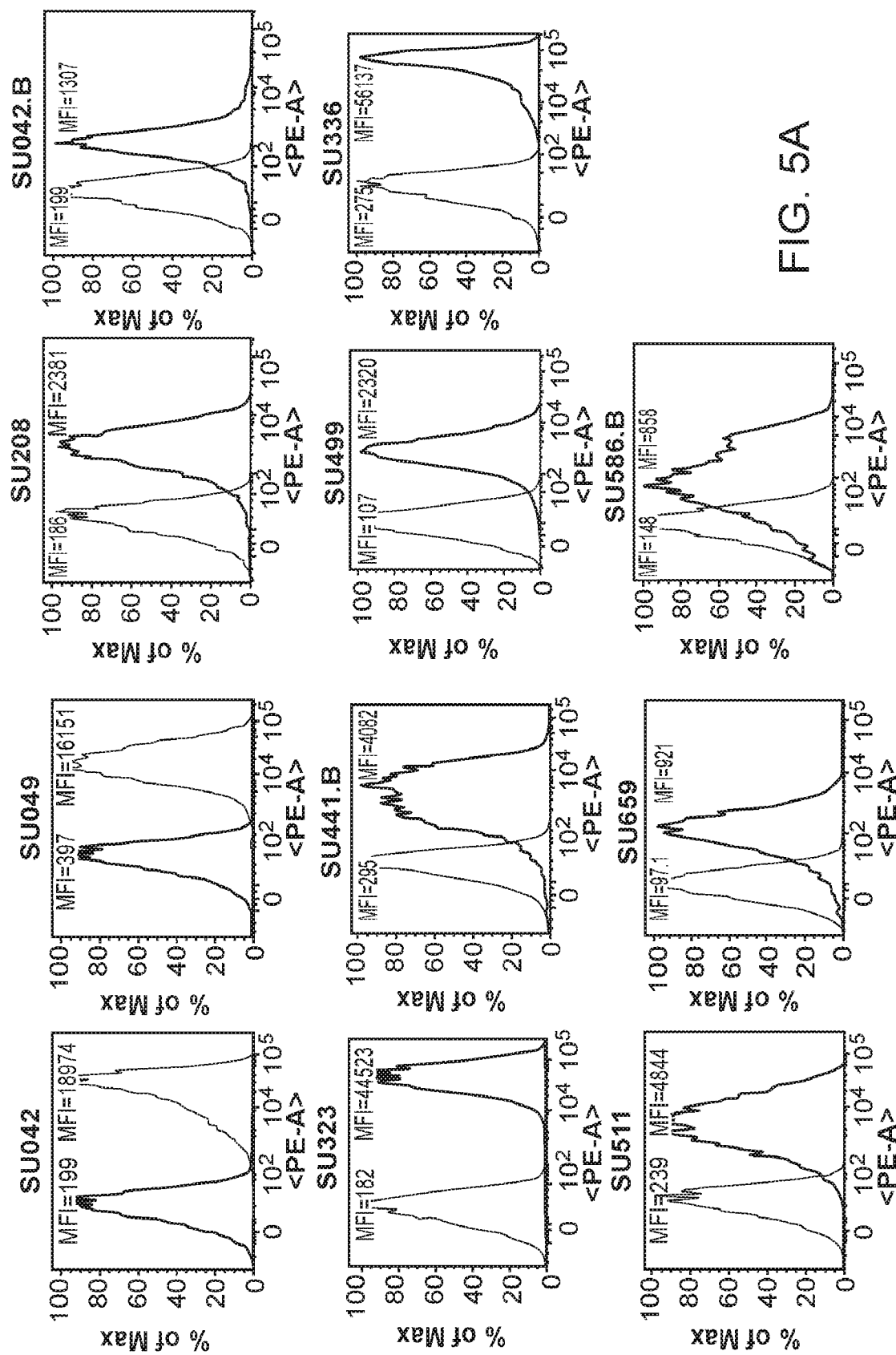
FIG. 5. CD93 expression on human primary rMLL AML samples (A) and other AML (B) cells. Human primary rMLL AML and other AML cells were stained with PE-conjugated anti-CD93 (blue) or an isotype antibody (red) and CD93 expression was measured by flow cytometry.
Figure 5B:
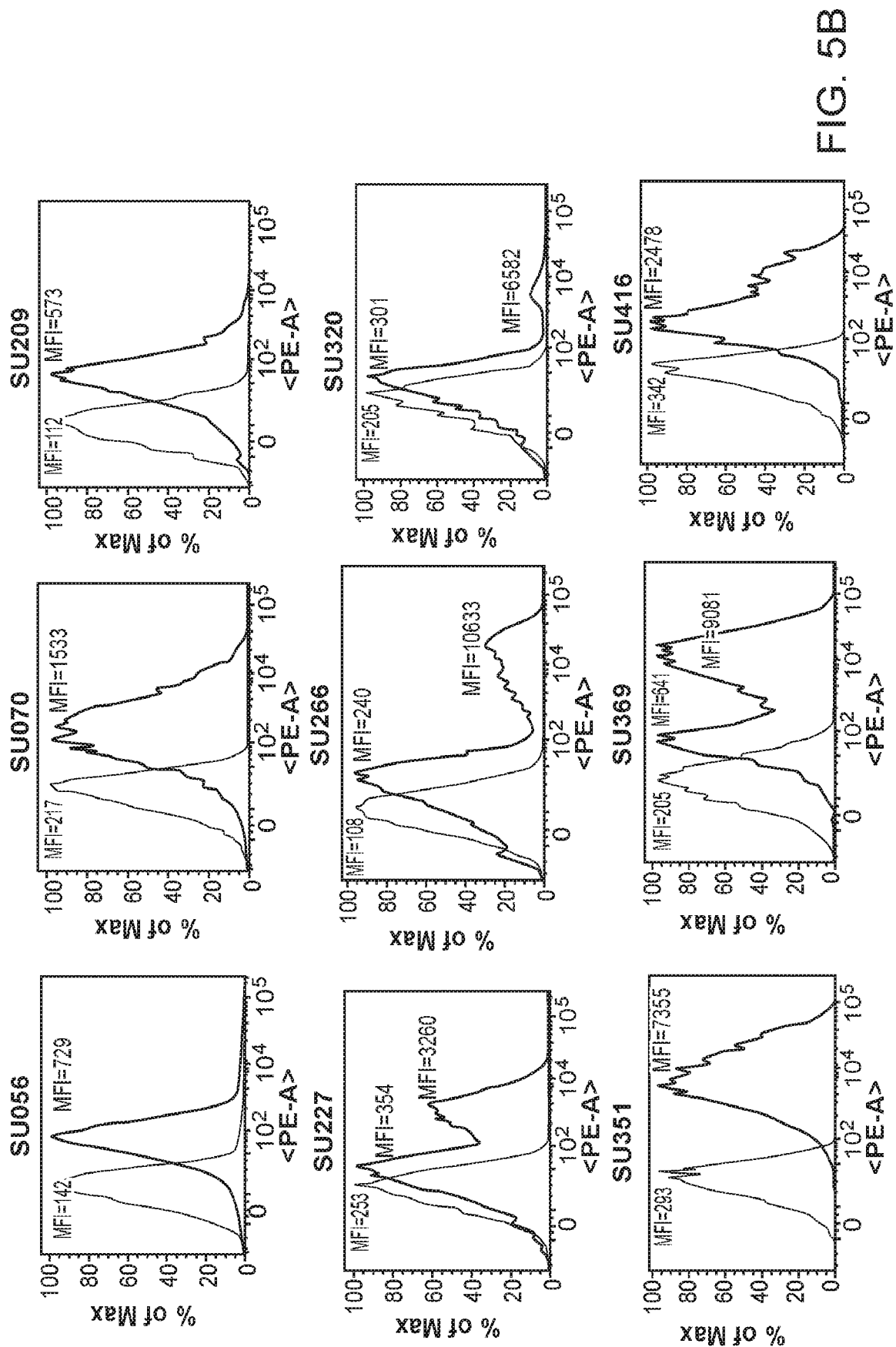
Figure 5B:
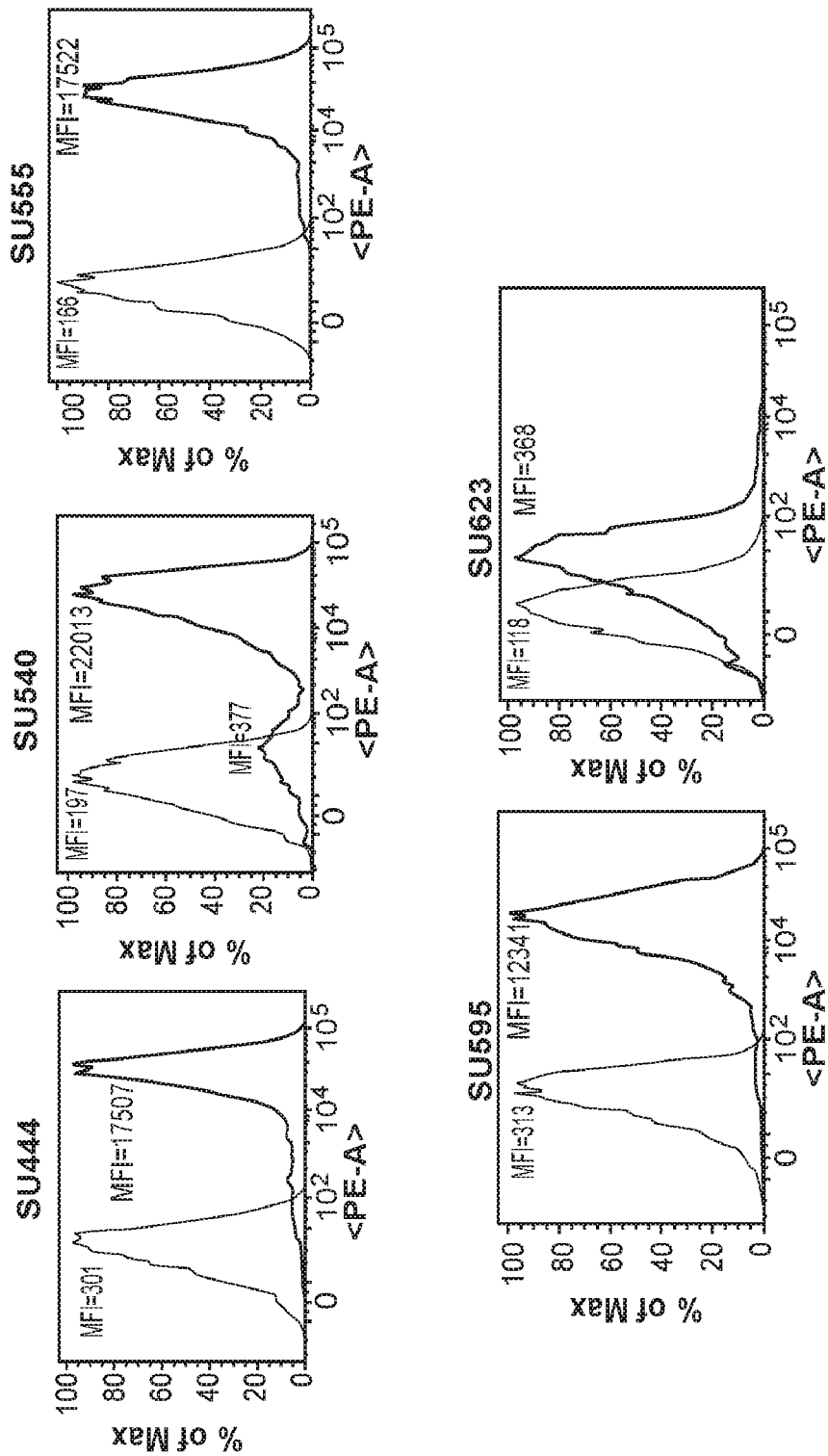

As shown, for example, in FIGS. 4 and 5, CD93 is expressed on the surface of a subset of some immune cells, including neutrophils and monocytes. It is expressed on the surface of primary leukemia cells, including AML and MLL cells.

Cancer. As used herein, the terms "cancer" (or "cancerous"), or "tumor" are used to refer to cells having the capacity for autonomous growth (e.g., an abnormal state or condition characterized by rapidly proliferating cell growth). Hyperproliferative and neoplastic disease states may be categorized as pathologic (e.g., characterizing or constituting a disease state), or they may be categorized as non-pathologic (e.g., as a deviation from normal but not associated with a disease state). The terms are meant to include all types of cancerous growths or oncogenic processes, metastatic tissues or malignantly transformed cells, tissues, or organs, irrespective of histopathologic type or stage of invasiveness. Pathologic hyperproliferative cells occur in disease states characterized by malignant tumor growth. Examples of non-pathologic hyperproliferative cells include proliferation of cells associated with wound repair. The terms "cancer" or "tumor" are also used to refer to malignancies of the various organ systems, including those affecting the lung, breast, thyroid, lymph glands and lymphoid tissue, gastrointestinal organs, and the genitourinary tract, as well as to adenocarcinomas which are generally considered to include malignancies such as most colon cancers, renal-cell carcinoma, prostate cancer and/or testicular tumors, non-small cell carcinoma of the lung, cancer of the small intestine and cancer of the esophagus.

Exemplary cancer types include but are not limited to AML, ALL, CML, adrenal cortical cancer, anal cancer, aplastic anemia, bile duct cancer, bladder cancer, bone cancer, bone metastasis, brain cancers, central nervous system (CNS) cancers, peripheral nervous system (PNS) cancers, breast cancer, cervical cancer, childhood Non-Hodgkin's lymphoma, colon and rectal cancer, endometrial cancer, esophagus cancer, Ewing's family of tumors (e.g., Ewing's sarcoma), eye cancer, gallbladder cancer, gastrointestinal carcinoid tumors, gastrointestinal stromal tumors, gestational trophoblastic disease, Hodgkin's lymphoma, Kaposi's sarcoma, kidney cancer, laryngeal and hypopharyngeal cancer, liver cancer, lung cancer, lung carcinoid tumors, Non-Hodgkin's lymphoma, male breast cancer, malignant mesothelioma, multiple myeloma, myelodysplastic syndrome, myeloproliferative disorders or neoplasms, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcomas, melanoma skin cancer, non-melanoma skin cancers, stomach cancer, testicular cancer, thymus cancer, thyroid cancer, uterine cancer (e.g. uterine sarcoma), transitional cell carcinoma, vaginal cancer, vulvar cancer, mesothelioma, squamous cell or epidermoid carcinoma, bronchial adenoma, choriocarinoma, head and neck cancers, teratocarcinoma, or Waldenstrom's macroglobulinemia.

The terms "hematological malignancy", "hematological tumor", and "hematological cancer" are used interchangeably and in the broadest sense herein and refer to all stages and all forms of cancer and hyperproliferative disorders arising from cells of the hematopoietic system.

Examples of hematologic malignancies that may be treated using the subject methods include leukemias, lymphomas, and myelomas, including but not limited to acute biphenotypic leukemia, acute myelogenous leukemia (AML), acute lymphoblastic leukemia (ALL), acute promyelocytic leukemia (APL), biphenotypic acute leukemia (BAL) blastic plasmacytoid dendritic cell neoplasm, chronic myelogenous leukemia (CML), chronic myelomonocytic leukemia (CMML), chronic lymphocytic leukemia (CLL) (called small lymphocytic lymphoma (SLL) when leukemic cells are absent), acute monocytic leukemia (AMOL), Hodgkin's lymphomas, Non-Hodgkin's lymphomas (e.g. chronic lymphocytic leukemia (CLL), diffuse large B-cell lymphoma (DLBCL), Follicular lymphoma (FL), Mantle cell lymphoma (MCL), Marginal zone lymphoma (MZL), Burkitt's lymphoma (BL), Hairy cell leukemia, Post-transplant lymphoproliferative disorder (PTLD), Waldenström's macroglobulinemia/lymphoplasmacytic lymphoma, hepatosplenic-T cell lymphoma, and cutaneous T cell lymphoma (including Sezary's syndrome)), multiple myeloma, myelodysplastic syndrome, and myeloproliferative neoplasms. In particular embodiments, the subject methods find utility in treatment of leukemias, e.g. acute biphenotypic leukemia, acute myelogenous leukemia (AML), acute lymphoblastic leukemia (ALL), acute promyelocytic leukemia, chronic myelogenous leukemia (CML), chronic myelomonocytic leukemia, chronic lymphocytic leukemia (CLL), acute monocytic leukemia (AMOL).

For AML, various molecular markers can find use in patient selection and dosing, including without limitation known clinical prognostic factors associated with favorable outcome include cytogenetic mutations such as t(15;17) PML/RARα, t(8;21)AML1/ETO, 11q23, and inv(16)CBFβ/MYH11, or molecular mutations in FLT3 associated with intermediate risk (e.g., FLT3-ITD, FLT3-D835), NPM1, EVI1, or cEBPα; clinical prognostic factors that have been associated with an intermediate outcome include but are not limited to normal karyotype, and the cytogenetic mutations +8, +21, +22, del(7q), and del(9q); and clinical prognostic factors that have been associated with an adverse outcome include but not limited to the cytogenetic mutations del(5q), 11q23, t(6;9), t(9;22), abnormal 3q, complex cytogenetics, and elevated expression levels of IL2Ra and/or MSI2. Response of MDS patients to therapy may be similar to the response of AML patients.

Myelodysplastic neoplasms (MDS) are a group of syndromes (preleukemia, refractory anemias, Ph-negative chronic myelocytic leukemia, chronic myelomonocytic leukemia, myeloid metaplasia) commonly seen in older patients. Exposure to carcinogens may by be implicated. MDS is characterized by clonal proliferation of hematopoietic cells, including erythroid, myeloid, and megakaryocytic forms. The bone marrow is normal or hypercellular, and ineffective hematopoiesis causes variable cytopenias, the most frequent being anemia. The disordered cell production is also associated with morphologic cellular abnormalities in marrow and blood. Extramedullary hematopoiesis may occur, leading to hepatomegaly and splenomegaly. Myelofibrosis is occasionally present at diagnosis or may develop during the course of MDS. The MDS clone is unstable and tends to progress to AML.

A hematologic malignancy suitable for treatment with the methods disclosed herein may comprise a mutation of the MLL gene. The MLL gene (myeloid/lymphoid leukemia or mixed lineage leukemia) also termed 'ALL-1,' 'HRX,' or 'Htrx' is rearranged in somatically acquired reciprocal translocations and in deletions and inversions at chromosomal band 11q23. These rearrangements occur in 5-10% of patients with acute lymphoblastic leukemia (ALL) or acute myeloid leukemia (AML) and in some patients with acute myelodysplastic syndrome (MDS). MLL is involved in the majority of both acute leukemias occurring in children under the age of 1 year and therapy-related AMLs. Neoplasms with MLL rearrangements are clinically aggressive and respond poorly to therapy.

Antigen binding domain (ABD). As used herein, the term ABD refers to a combination of variable heavy (VH and variable light (VL) polypeptides to associate to form a variable region domain. An ABD is the minimum antibody fragment that contains a complete antigen-recognition and binding site. This region consists of heavy- and one light-chain variable domain in tight, non-covalent association, as a single polypeptide or as a dimer. It is in this configuration that the three CDRS of each variable domain interact to define an antigen-binding site on the surface of the domain. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The VL and VH sequences disclosed herein are derived from antibodies, but can be reformatted as fragments, as single chain binding domains, linked to chimeric antigen receptors, and the like. Exemplary VH and VL sequences are provided herein as SEQ ID NO:1 and SEQ ID NI:6 (mouse); and as SEQ ID NO:2 and SEQ ID NO:7 (humanized); and CDR sequences are defined for each, where the VH CDRs are SEQ ID NO:3, 4, 5 and the VL CDRs are SEQ ID NO:8, 9, 10.

The terms "antibodies" and "immunoglobulin" include antibodies or immunoglobulins of any isotype, fragments of antibodies that retain specific binding to antigen, including, but not limited to, Fab, Fv, scFv, and Fd fragments, chimeric antibodies, humanized antibodies, single-chain antibodies (scAb), single domain antibodies (dAb), single domain heavy chain antibodies, a single domain light chain antibodies, bispecific antibodies, multi-specific antibodies, and fusion proteins comprising an antigen-binding portion of an antibody and a non-antibody protein. Antibodies can be detectably labeled, e.g., with a radioisotope, an enzyme that generates a detectable product, a fluorescent protein, and the like. Antibodies can be further conjugated to other moieties, such as members of specific binding pairs, e.g., biotin (member of biotin-avidin specific binding pair), and the like. Also encompassed by the term are Fab', Fv, F(ab')$_2$, and or other antibody fragments that retain specific binding to antigen, and monoclonal antibodies. As used herein, a monoclonal antibody is an antibody produced by a group of identical cells, all of which were produced from a single cell by cellular replication. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "humanized immunoglobulin" as used herein refers to an immunoglobulin comprising portions of immunoglobulins of different origin, wherein at least one portion comprises amino acid sequences of human origin. A chimeric antibody can comprise portions derived from an immunoglobulin of nonhuman origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). A humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). Chimeric or CDR-grafted single chain antibodies are also encompassed by the term humanized immunoglobulin.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); domain antibodies (dAb; Holt et al. (2003) *Trends Biotechnol.* 21:484); single-chain antibody molecules; and multi-specific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

The "Fab" fragment also contains the constant domain of the light chain and the first constant domain (CH$_1$) of the heavy chain. Fab fragments differ from Fab' fragments by the addition of a few residues at the carboxyl terminus of the heavy chain CH$_1$ domain including one or more cysteines from the antibody hinge region. Fab'-SH is the designation for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

"Single-chain Fv" (scFv) polypeptides comprise the $V_H$ and $V_L$ domains of an antibody, where these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun in *The Pharmacology of Monoclonal Antibodies, vol. 113, Rosenburg and Moore eds., Springer-Verlag, New York, pp.* 269-315 (1994).

Chimeric antigen receptor (CAR). A CAR is comprised of the general structure where an antigen binding domain, e.g. an anti-CD93 ABD disclosed herein, usually provided in an scFv format, is linked to T cell receptor effector functions. The term refers to artificial multi-module molecules capable of triggering or inhibiting the activation of an immune cell. Exemplary CARs are diagrammed in FIG. 7A. A CAR will generally comprise an anti-CD93 ABD as described herein, linker, transmembrane domain and cytoplasmic signaling domain. In some instances, a CAR will include one or more co-stimulatory domains and/or one or more co-inhibitory domains.

A spacer (linker) region links the antigen binding domain to the transmembrane domain. It should be flexible enough to allow the antigen binding domain to orient in different directions to facilitate antigen recognition. The simplest form is the hinge region from an immunoglobulin, e.g. the hinge from any one of IgG1, IgG2a, IgG2b, IgG3, IgG4, particularly the human protein sequences. Alternatives include the CH2CH3 region of immunoglobulin and portions of CD3. For many scFv based constructs, an IgG hinge is effective. In some embodiments the linker comprises the amino acid sequence $(G_4S)_n$ where n is 1, 2, 3, 4, 5, etc., and in some embodiments n is 3.

The CAR transmembrane domain (TM) is frequently derived from type I membrane proteins, such as CD3ζ, CD4, CD8, CD28, etc.

A cytoplasmic signaling domain, such as those derived from the T cell receptor ζ-chain, is employed as part of the CAR in order to produce stimulatory signals for T lymphocyte proliferation and effector function following engagement of the chimeric receptor with the target antigen. Endodomains from co-stimulatory molecules may be included in the cytoplasmic signaling portion of the CAR.

The term "co-stimulatory domain", refers to a stimulatory domain, typically an endodomain, of a CAR that provides a secondary non-specific activation mechanism through which a primary specific stimulation is propagated. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies. Nat Rev Immunol (2013) 13(4):227-42, the disclosure of which are incorporated herein by reference in their entirety. Non-limiting examples of suitable co-stimulatory polypeptides include, but are not limited to, 4-1BB (CD137), CD28, ICOS, OX-40, BTLA, CD27, CD30, GITR, and HVEM.

The term "co-inhibitory domain" refers to an inhibitory domain, typically an endodomain, derived from a receptor that provides secondary inhibition of primary antigen-specific activation mechanisms which prevents co-stimulation. Co-inhibition, e.g., T cell co-inhibition, and the factors involved have been described in Chen & Flies. *Nat Rev Immunol* (2013) 13(4):227-42 and Thaventhiran et al. *J Clin Cell Immunol* (2012) S12. In some embodiments, co-inhibitory domains homodimerize. A co-inhibitory domain can be an intracellular portion of a transmembrane protei. Non-limiting examples of suitable co-inhibitory polypeptides include, but are not limited to, CTLA-4 and PD-1.

A first-generation CAR transmits the signal from antigen binding through only a single signaling domain, for example a signaling domain derived from the high-affinity receptor for IgE FcεRIγ, or the CD3ζ chain. The domain contains one or three immunoreceptor tyrosine-based activating motif(s) [ITAM(s)] for antigen-dependent T-cell activation. The ITAM-based activating signal endows T-cells with the ability to lyse the target tumor cells and secret cytokines in response to antigen binding.

Second-generation CARs include a co-stimulatory signal in addition to the CD3ζ signal. Coincidental delivery of the delivered co-stimulatory signal enhances cytokine secretion and antitumor activity induced by CAR-transduced T-cells. The co-stimulatory domain is usually be membrane proximal relative to the CD3ζ domain. Third-generation CARs include a tripartite signaling domain, comprising for example a CD28, CD3ζ, OX40 or 4-1BB signaling region. In fourth generation, or "armored car" CAR T-cells are further gene modified to express or block molecules and/or receptors to enhance immune activity.

CAR variants include split CARs wherein the extracellular portion, the ABD and the cytoplasmic signaling domain of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR molecules and derivatives thereof (i.e., CAR variants) are described, e.g., in PCT Application Nos. US2014/016527, US1996/017060, US2013/063083; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

CAR variants also include bispecific or tandem CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. Tandem CARs (TanCAR) mediate bispecific activation of T cells through the engagement of two chimeric receptors designed to deliver stimulatory or costimulatory signals in response to an independent engagement of two different tumor associated antigens. iCARs use the dual antigen targeting to shout down the activation of an active CAR through the engagement of a second suppressive receptor equipped with inhibitory signaling domains The dual recognition of different epitopes by two CARs diversely designed to either deliver killing through ζ-chain or costimulatory signals, e.g. through CD28 allows a more selective activation of the reprogrammed T cells by restricting Tandem CAR's activity to cancer cell expressing simultaneously two antigens rather than one. The potency of delivered signals in engineered T cells will remain below threshold of activation and thus ineffective in absence of the engagement of costimulatory receptor. The combinatorial antigen recognition enhances selective tumor eradication and protects normal tissues expressing only one antigen from unwanted reactions.

Inhibitory CARs (iCARs) are designed to regulate CAR-T cells activity through inhibitory receptors signaling modules activation. This approach combines the activity of two CARs, one of which generates dominant negative signals limiting the responses of CAR-T cells activated by the activating receptor. iCARs can switch off the response of the counteracting activator CAR when bound to a specific antigen expressed only by normal tissues. In this way, iCARs-T cells can distinguish cancer cells from healthy ones, and reversibly block functionalities of transduced T cells in an antigen-selective fashion. CTLA-4 or PD-1 intracellular domains in iCARs trigger inhibitory signals on T lymphocytes, leading to less cytokine production, less efficient target cell lysis, and altered lymphocyte motility.

An anti-CD93 ADP can be provided as a "chimeric bispecific binding member", i.e. a chimeric polypeptide having dual specificity to two different binding partners (e.g., two different antigens). The second antigen may be, for example, a tumor associated antigen present on leukemia cells e.g. CD123, FLT3, TIM3, CD99, CD96, B7-H3, CD33, IL1RAP, CLL1 (CLEC12A) etc. Non-limiting examples of chimeric bispecific binding members include bispecific antibodies, bispecific conjugated monoclonal antibodies $(mab)_2$, bispecific antibody fragments (e.g., $F(ab)_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. MAbs. (2012) 4(2): 182-197; Stamova et al. Antibodies 2012, 1(2), 172-198; Farhadfar et al. Leuk Res. (2016) 49:13-21; Benjamin et al. Ther Adv Hematol. (2016) 7(3):142-56; Kiefer et al. Immunol Rev. (2016) 270(1):178-92; Fan et al. J Hematol Oncol. (2015) 8:130; May et al. Am J Health Syst Pharm. (2016) 73(1):e6-e13; the disclosures of which are incorporated herein by reference in their entirety.

In some instances, a chimeric bispecific binding member may be a bispecific T cell engager (BiTE). A BiTE is generally made by fusing a specific binding member (e.g., a scFv) that binds an antigen to a specific binding member (e.g., a scFv) with a second binding domain specific for a T cell molecule such as CD3.

In some instances, a chimeric bispecific binding member may be a CAR T cell adapter. As used herein, by "CAR T cell adapter" is meant an expressed bispecific polypeptide that binds the antigen recognition domain of a CAR and redirects the CAR to a second antigen. Generally, a CAR T cell adapter will have to binding regions, one specific for an epitope on the CAR to which it is directed and a second epitope directed to a binding partner which, when bound, transduces the binding signal activating the CAR. Useful CAR T cell adapters include but are not limited to e.g., those described in Kim et al. J Am Chem Soc. (2015) 137(8): 2832-5; Ma et al. Proc Natl Acad Sci USA. (2016) 113(4): E450-8 and Cao et al. Angew Chem Int Ed Engl. (2016) 55(26):7520-4; the disclosures of which are incorporated herein by reference in their entirety.

Effector anti-CD93 CAR-T cells include autologous or allogeneic immune cells having cytolytic activity against a target cell expressing CD93, including hematologic malignant cells. The effector cells have cytolytic activity that does not require recognition through the T cell antigen receptor. In some embodiments, a T cell is engineered to express an anti-CD93 CAR. The term "T cells" refers to mammalian immune effector cells that may be characterized by expression of CD3 and/or T cell antigen receptor.

In some embodiments, the engineered cells comprise a complex mixture of immune cells, e.g., tumor infiltrating lymphocytes (TILs) isolated from an individual in need of treatment. See, for example, Yang and Rosenberg (2016) Adv Immunol. 130:279-94, "Adoptive T Cell Therapy for Cancer; Feldman et al (2015) Semin Oncol. 42(4):626-39 "Adoptive Cell Therapy-Tumor-Infiltrating Lymphocytes, T-Cell Receptors, and Chimeric Antigen Receptors"; Clinical Trial NCT01174121, "Immunotherapy Using Tumor Infiltrating Lymphocytes for Patients With Metastatic Cancer"; Tran et al. (2014) Science 344(6184)641-645, "Cancer immunotherapy based on mutation-specific CD4+ T cells in a patient with epithelial cancer".

In other embodiments, the engineered T cell is allogeneic with respect to the individual that is treated, e.g. see clinical trials NCT03121625; NCT03016377; NCT02476734; NCT02746952; NCT02808442. See for review Graham et al. (2018) Cells. 7(10) E155. In some embodiments an allogeneic engineered T cell is fully HLA matched. However not all patients have a fully matched donor and a cellular product suitable for all patients independent of HLA type provides an alternative. A universal 'off the shelf' CAR T cell product provides advantages in uniformity of harvest and manufacture.

Allogeneic T cells can be genetically modified to reduce graft v host disease. For example the TCRαβ receptor can be knocked out by different gene editing techniques. TCRαβ is a heterodimer and both alpha and beta chains need to be present for it to be expressed. A single gene codes for the alpha chain (TRAC), whereas there are 2 genes coding for the beta chain, therefore TRAC loci KO has been deleted for this purpose. A number of different approaches have been used to accomplish this deletion, e.g. CRISPR/Cas9; meganuclease; engineered I-CreI homing endonuclease, etc. See, for example, Eyquem et al. (2017) Nature 543:113-117, in which the TRAC coding sequence is replaced by the CAR coding sequence; and Georgiadis et al. (2018) Mol. Ther. 26:1215-1227, which linked CAR expression with TRAC disruption by clustered regularly interspaced short palindromic repeats (CRISPR)/Cas9 without directly incorporating the CAR into the TRAC loci. An alternative strategy to prevent GVHD modifies CAR-T cells to express an inhibitor of TCRαβ signaling, for example using a truncated form of CD3ζ as a TCR inhibitory molecule.

Allogeneic T cells may be administered in combination with intensification of lymphodepletion to allow CAR-T cells to expand and clear malignant cells prior to host immune recovery, e.g. by administration of Alemtuzumab (monoclonal anti-CD52), purine analogs, etc. The allogeneic T cells may be modified for resistance to Alemtuzumab, and currently in clinical trials. Gene editing has also been used to prevent expression of HLA class I molecules on CAR-T cells, e.g. by deletion of β2-microglobulin, see NCT03166878.

In addition to modifying T cells, induced pluripotent stem (iPS) CAR-T cells can provide a source of allogeneic CAR-T cells. For example, transducing donor T cells with reprogramming factors can restore pluripotency, and are then re-differentiated to T effector cells.

T cells for engineering as described above collected from a subject or a donor may be separated from a mixture of cells by techniques that enrich for desired cells, or may be engineered and cultured without separation. An appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Techniques for affinity separation may include magnetic separation, using antibody-coated magnetic beads, affinity chromatography, cytotoxic agents joined to a monoclonal antibody or used in conjunction with a monoclonal antibody, e.g., complement and cytotoxins, and "panning" with antibody attached to a solid matrix, e.g., a plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the selected cells. The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum (FCS).

The collected and optionally enriched cell population may be used immediately for genetic modification, or may be frozen at liquid nitrogen temperatures and stored, being thawed and capable of being reused. The cells will usually be stored in 10% DMSO, 50% FCS, 40% RPMI 1640 medium.

The engineered cells may be infused to the subject in any physiologically acceptable medium by any convenient route of administration, normally intravascularly, although they may also be introduced by other routes, where the cells may find an appropriate site for growth. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of T cells that are obtained during collection.

Expression construct: The anti-CD93 ABD construct (e.g. CAR, antibody, scFv, etc.) coding sequence may be introduced on an expression vector into a cell to be engineered. For example, a CAR coding sequence may be introduced into the site of the endogenous T cell receptor, e.g. TRAC gene, e.g., using CRISPR technology (see, for example Eyquem et al. (2017) Nature 543:113-117; Ren et al. (2017) Protein & Cell 1-10; Ren et al. (2017) Oncotarget 8(10): 17002-17011). CRISPR/Cas9 system can be directly applied to human cells by transfection with a plasmid that encodes Cas9 and sgRNA. The viral delivery of CRISPR components has been extensively demonstrated using lentiviral and retroviral vectors. Gene editing with CRISPR encoded by non-integrating virus, such as adenovirus and adenovirus-associated virus (AAV), has also been reported. Recent discoveries of smaller Cas proteins have enabled and enhanced the combination of this technology with vectors that have gained increasing success for their safety profile and efficiency, such as AAV vectors.

The nucleic acid encoding an anti-CD93 ABD construct is inserted into a vector for expression and/or integration. Many such vectors are available. The vector components generally include, but are not limited to, one or more of the following: an origin of replication, one or more marker genes, an enhancer element, a promoter, and a transcription termination sequence. Vectors include viral vectors, plasmid vectors, integrating vectors, and the like.

Expression vectors may contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Nucleic acids are "operably linked" when placed into a functional relationship with another nucleic acid sequence. For example, DNA for a signal sequence is operably linked to DNA for a polypeptide if it is expressed as a preprotein that signals the secretion of the polypeptide; a promoter or enhancer is operably linked to a coding sequence if it affects the transcription of the sequence; and a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous.

Expression vectors will contain a promoter that is recognized by the host organism and is operably linked to the anti-CD93 ABD construct coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus LTR (such as murine stem cell virus), hepatitis-B virus and Simian Virus 40 (SV40), from heterologous mammalian promoters, e.g., the actin promoter, PGK (phosphoglycerate kinase), or an immunoglobulin promoter, or from heat-shock promoters, provided such promoters are compatible with the host cell systems. The early and late promoters of the SV40 virus are conveniently obtained as an SV40 restriction fragment that also contains the SV40 viral origin of replication.

Transcription by higher eukaryotes may be increased by inserting an enhancer sequence into the vector. Enhancers are cis-acting elements of DNA, usually about from 10 to 300 bp in length, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors for use in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

Suitable host cells for cloning or expressing an anti-CD93 ABD construct are the prokaryotic, yeast, or other eukaryotic cells described above. Examples of useful mammalian host cell lines are mouse L cells (L-M[TK-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse Sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells, including T cells, stem cells, etc. can be transfected with the above-described expression vectors for anti-CD93 ABD construct expression. Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "sequence identity," as used herein in reference to polypeptide or DNA sequences, refers to the subunit sequence identity between two molecules. When a subunit position in both of the molecules is occupied by the same monomeric subunit (e.g., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990).

By "protein variant" or "variant protein" or "variant polypeptide" herein is meant a protein that differs from a wild-type protein by virtue of at least one amino acid modification. The parent polypeptide may be a naturally occurring or wild-type (WT) polypeptide, or may be a modified version of a WT polypeptide. Variant polypeptide may refer to the polypeptide itself, a composition comprising the polypeptide, or the amino sequence that encodes it. Preferably, the variant polypeptide has at least one amino acid modification compared to the parent polypeptide, e.g. from about one to about ten amino acid modifications, and preferably from about one to about five amino acid modifications compared to the parent.

By "parent polypeptide", "parent protein", "precursor polypeptide", or "precursor protein" as used herein is meant an unmodified polypeptide that is subsequently modified to generate a variant. A parent polypeptide may be a wild-type (or native) polypeptide, or a variant or engineered version of a wild-type polypeptide. Parent polypeptide may refer to the polypeptide itself, compositions that comprise the parent polypeptide, or the amino acid sequence that encodes it.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogs" refers to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acid modifications disclosed herein may include amino acid substitutions, deletions and insertions, particularly amino acid substitutions. Variant proteins may also include conservative modifications and substitutions at other positions of the cytokine and/or receptor (e.g., positions other than those involved in the affinity engineering). Such conservative substitutions include those described by Dayhoff in The Atlas of Protein Sequence and Structure 5 (1978), and by Argos in EMBO J., 8:779-785 (1989). For example, amino acids belonging to one of the following groups represent conservative changes: Group I: Ala, Pro, Gly, Gln, Asn, Ser, Thr; Group II: Cys, Ser, Tyr, Thr; Group III: Val, Ile, Leu, Met, Ala, Phe; Group IV: Lys, Arg, His; Group V: Phe, Tyr, Trp, His; and Group VI: Asp, Glu. Further, amino acid substitutions with a designated amino acid may be replaced with a conservative change.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In some embodiments, the mammal is a human. The terms "subject," "individual," and "patient" encompass, without limitation, individuals having a disease. Subjects may be human, but also include other mammals, particularly those mammals useful as laboratory models for human disease, e.g., mice, rats, etc.

The term "sample" with reference to a patient encompasses blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

The term "diagnosis" is used herein to refer to the identification of a molecular or pathological state, disease or condition in a subject, individual, or patient.

The term "prognosis" is used herein to refer to the prediction of the likelihood of death or disease progression, including recurrence, spread, and drug resistance, in a subject, individual, or patient. The term "prediction" is used herein to refer to the act of foretelling or estimating, based on observation, experience, or scientific reasoning, the likelihood of a subject, individual, or patient experiencing a particular event or clinical outcome. In one example, a physician may attempt to predict the likelihood that a patient will survive.

As used herein, the terms "treatment," "treating," and the like, refer to administering an agent, or carrying out a procedure, for the purposes of obtaining an effect on or in a subject, individual, or patient. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of cancer in a mammal, particularly in a human, and includes: (a) inhibiting the disease, i.e., arresting its development; and (b) relieving the disease or its symptoms, i.e., causing regression of the disease or its symptoms.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of engineered cells to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

As used herein, a "therapeutically effective amount" refers to that amount of the therapeutic agent, e.g. an infusion of engineered T cells, and antibody construct, etc., sufficient to treat or manage a disease or disorder. A therapeutically effective amount may refer to the amount of therapeutic agent sufficient to delay or minimize the onset of disease, e.g., to delay or minimize the growth and wspread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"In combination with", "combination therapy" and "combination products" refer, in certain embodiments, to the concurrent administration to a patient of the engineered proteins and cells described herein in combination with additional therapies, e.g. surgery, radiation, chemotherapy, and the like. When administered in combination, each component can be administered at the same time or sequentially in any order at different points in time. Thus, each component can be administered separately but sufficiently closely in time so as to provide the desired therapeutic effect.

"Concomitant administration" means administration of one or more components, such as engineered proteins and cells, known therapeutic agents, etc. at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Chemotherapeutic agents that can be administered in combination with an anti-CD93 ABD polypeptide or engineered cell include, without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Targeted therapeutics that can be administered in combination with an anti-CD93 ABD polypeptide or engineered cell may include, without limitation, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade), Jakafi (ruxolitinib); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt), IDH inhibitors, such as AG-221, PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar).

An anti-CD93 ABD polypeptide or engineered cell may be administered in combination with an immunomodulator, such as a cytokine, a lymphokine, a monokine, a stem cell growth factor, a lymphotoxin (LT), a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), such as TGF-α or TGF-β, insulin-like growth factor (IGF), erythropoietin, thrombopoietin, a tumor necrosis factor (TNF) such as TNF-α or TNF-β, a mullerian-inhibiting substance, mouse gonadotropin-associated peptide, inhibin, activin, vascular endothelial growth factor, integrin, granulocyte-colony stimulating factor (G-CSF), granulocyte macrophage-colony stimulating factor (GM-CSF), an interferon such as interferon-α, interferon-β, or interferon-γ, S1 factor, an interleukin (IL) such as IL-1, 1L-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 or IL-25, LIF, kit-ligand, FLT-3, angiostatin, thrombospondin, endostatin, and LT.

Tumor specific monoclonal antibodies that can be administered in combination with an anti-CD93 ABD polypeptide or engineered cell may include, without limitation, Rituximab (marketed as MabThera or Rituxan), Alemtuzumab, Panitumumab, Ipilimumab (Yervoy), etc.

Of interest are hypomethylating (also known as epigenetic) agents for combination with an anti-CD93 ABD polypeptide or engineered cell. A hypomethylating agent is a drug that inhibits DNA methylation. Currently available hypomethylating agents block the activity of DNA methyltransferase (DNA methyltransferase inhibitors/DNMT inhibitors). Currently two members of the class, azacitidine and decitabine are FDA-approved for use in the United States. Guadecitabine is also of interest. Because of their relatively mild side effects, azacitidine and decitabine are particularly feasible for the treatment of older patients and patients with co-morbidities. Both drugs have remarkable activity against AML blasts with unfavorable cytogenetic characteristics.

Treatment of hematologic malignancies, e.g. leukemias, can be combined with one or more therapeutic entities. In some embodiments, the additional therapeutic entity in an immune response modulator. Immune checkpoint proteins are immune inhibitory molecules that act to decrease immune responsiveness toward a target cell, particularly against a tumor cell in the methods of the invention. Endogenous responses to tumors by T cells can be dysregulated by tumor cells activating immune checkpoints (immune inhibitory proteins) and inhibiting co-stimulatory receptors (immune activating proteins). The class of therapeutic agents referred to in the art as "immune checkpoint inhibitors" reverses the inhibition of immune responses through administering antagonists of inhibitory signals. Other immunotherapies administer agonists of immune costimulatory molecules to increase responsiveness.

The immune-checkpoint receptors that have been most actively studied in the context of clinical cancer immunotherapy, cytotoxic T-lymphocyte-associated antigen 4 (CTLA4; also known as CD152) and programmed cell death protein 1 (PD1; also known as CD279)—are both inhibitory receptors. The clinical activity of antibodies that block either of these receptors implies that antitumor immunity can be enhanced at multiple levels and that combinatorial strategies can be intelligently designed, guided by mechanistic considerations and preclinical models.

Polypeptide and Polynucleotide Compositions

Polypeptide constructs and compositions are provided, which comprise an anti-CD93 ABD linked to an effector polypeptide, which effector polypeptide may include, without limitation, chimeric antigen receptors; antibodies; and fragments and derivatives thereof, which polypeptides may be referred to as an anti-CD93 ABD construct. Such constructs comprise an anti-CD93 ABD having one or both of a variable heavy (VH) and a variable light (VL) domain polypeptide, where a VH polypeptide comprises least one, at least two, up to 3 VH CDR sequences as provided herein and as set forth in SEQ ID NO:3, 4 and 5; and a VL polypeptide comprises least one, at least two, up to 3 VL CDR sequences as provided herein and as set forth in SEQ ID NO: 8, 9 and 10, in combination with framework sequences from a variable region, e.g. human VH or VL framework sequences.

In some embodiments an anti-CD93 ABD comprises at least one VL sequence comprising the 3 light chain CDR sequences provided herein, situated in a variable region framework, which may be, without limitation, a human or mouse variable region framework, and at least one VH sequence comprising the 3 heavy chain CDR sequence provided herein, situated in a variable region framework, which may be, without limitation, a human or mouse variable region framework.

In some embodiments, the anti-CD93 ABD comprises an amino acid sequence variant of one or more of the CDRs of the provided VH and VL sequences, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally have a binding affinity for human CD93 of at least about $10^{-8}$ M and will bind to the same epitope as an anti-CD93 ABD having the amino acid sequence of those set forth herein.

In some embodiments a polypeptide of interest has a contiguous sequence of at least about 10 amino acids, at least about 15 amino acids, at least about 20 amino acids, at least about 25 amino acids, at least about 30 amino acids, up to the complete provided variable region as set forth in SEQ ID NO:1, 2, 6 or 7. Polypeptides of interest also include variable regions sequences that differ by up to one, up to two, up to 3, up to 4, up to 5, up to 6 or more amino acids as compared to the amino acids sequence set forth set forth in SEQ ID NO:1, 2, 6 or 7. In other embodiments a polypeptide of interest is at least about 80%, at least about 85%, at least about 90%, at least about 95%, at least about 99% identical to the amino acid sequence set forth set forth in SEQ ID NO:1, 2, 6 or 7.

In an embodiment, the anti-CD93 ABD is covalently linked, e.g. as a single polypeptide fused in frame to an effector polypeptide of a CAR. In some embodiments, the anti-CD93 ABD of a CAR is a single chain variable region. In some embodiments the anti-CD93 ABD comprises humanized variable region sequences. In some embodiments an anti-CD93 CAR is expressed by a human T cell. In some embodiments an anti-CD93 CAR is a bi-specific CAR, where a second antigenic specificity may be an antigen present on hematologic malignant cells, e.g. CD123, FLT3, TIM3, CD99, CD96, B7-H3, etc. In other embodiments an engineered T cell expresses an anti-CD93 CAR and a second CAR with specificity for an antigen present on hematologic malignant cells.

In an embodiment the anti-CD93 ABD is provided as a polypeptide linked to an immunoglobulin effector sequence, for example as an scFv, as a full length chimeric or humanized antibody, e.g. having a human immunoglobulin constant region of any isotype, e.g. IgG1, IgG2, IgG3, IgG4, IgA, etc., or an antibody fragment, e.g. a F(ab')$_2$ fragment, and F(ab) fragment, etc. In addition to Fabs, smaller antibody fragments and epitope-binding peptides having binding specificity for at least one epitope of CD93 are also contemplated by the present invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form. An anti-CD93 antibody may be labeled with a detectable label, immobilized on a solid phase and/or conjugated with a heterologous compound. The antibody may also be provided as a bi-specific or multispecific antibody reactive with a second antigen, particularly including other cancer antigens e.g. CD123, FLT3, TIM3, CD99, CD96, B7-H3, etc.; or with immunotherapy reagents, e.g. anti-PD-1/PD-L1, anti-CTLA-4, anti-CD40, anti-CD47, and the like.

Also provided are isolated nucleic acids encoding the anti-CD93 ABD and constructs thereof, vectors and host cells comprising the nucleic acid, and recombinant techniques for the production of the polypeptide constructs. Nucleic acids of interest encode a polypeptide that is at least about 80% identical to the provided polypeptide sequences, at least about 85%, at least about 90%, at least about 95%, at least about 99%, or identical. Polynucleotide sequences may encode any or all of the provided CDR sequences, or may encode a complete variable region, an scFv, a complete polypeptide construct such as a CAR, and antibody, and the like. As is known in the art, a variable region sequence may be fused to any appropriate constant region sequence.

In some embodiments, a vector comprising a coding sequence that encodes an anti-CD93 ABD or anti-CD93 ABD construct is provided, where the coding sequence is operably linked to a promoter active in the desired cell; or is provided in a vector suitable for genomic insertion, e.g., by CRISPR. Various vectors are known in the art and can be used for this purpose, e.g., viral vectors, plasmid vectors, minicircle vectors, which vectors can be integrated into the target cell genome, or can be episomally maintained.

Polypeptide compositions may be prepared as injectables, either as liquid solutions or suspensions; solid forms suitable for solution in, or suspension in, liquid vehicles prior to injection can also be prepared. Proteins can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In another embodiment of the invention, an article of manufacture containing in isolated polypeptide or polynucleotide is provided. The article of manufacture comprises a container and a label. Suitable containers include, for example, bottles, vials, syringes, and test tubes. The containers may be formed from a variety of materials such as glass or plastic. The container holds a polypeptide or polynucleotide composition, which may be a therapeutic composition, e.g. for treatment of cancer, and may have a sterile access port (for example the container may be an intravenous solution bag or a vial having a stopper pierceable by a hypodermic injection needle). A label on or associated with the container may indicate that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

Cell Compositions

In some embodiments, an engineered cell is provided, in which the cell has been modified by introduction of an anti-CD93 CAR. In some embodiments the cell is a T cell, including without limitation naïve CD8+ T cells, cytotoxic CD8+ T cells; etc. In other embodiments, the engineered cell is a stem cell, e.g. a hematopoietic stem cell, or an iPSC. In some embodiments, the cell is genetically modified in an ex vivo procedure, prior to transfer into a subject. The engineered cell can be provided in a unit dose for therapy, and can be allogeneic, autologous, etc. with respect to an intended recipient.

Methods may include a step of obtaining desired cells, e.g., T cells, hematopoietic stem cells, etc., which may be isolated from a biological sample, or may be derived in vitro from a source of progenitor cells, e.g. iPSC. The cells are transduced or transfected with a vector comprising a sequence encoding the receptor, which step may be performed in any suitable culture medium. As discussed above, the vector may integrate a CAR coding sequence into the genomic site of a TCR chain, e.g. the TCRA site, or may provide for expression from an exogenous promoter.

For example, cells may be collected from a cancer patient, modified ex vivo to express an anti-CD93 CAR, and reintroduced into the subject. The cells collected from the subject may be collected from any convenient and appropriate source, including e.g., peripheral blood (e.g., the subject's peripheral blood), a biopsy (e.g., a tumor biopsy from the subject), and the like. In some instances, the cells collected may be tumor infiltrating lymphocytes (TILs), e.g., TILs collected from a tumor of a subject.

Where the use of autologous cells is not desirable, e.g. where a patient has insufficient T cells for modification, where there is insufficient time to expand autologous cells, etc., allogeneic cells may be used, e.g. T cells or stem cells from a healthy donor. As discussed herein, such allogeneic cells can be genetically modified to reduce GVHD, to reduce host versus graft responses, etc.

In some instances, modification of cells to generate CAR-T cells will be limited to introduction of an anti-CD93 CAR. In other instances, the T cell is modified to express a second CAR, e.g. a tandem CAR, an iCAR, and the like. The second CAR can provide for greater specificity to tumor cells, by reducing activity of the CAR-T cell to normal cells expressing CD93.

Engineered cells can be provided in pharmaceutical compositions suitable for therapeutic use, e.g. for human treatment. Therapeutic formulations comprising such cells can be frozen, or prepared for administration with physiologically acceptable carriers, excipients or stabilizers (Remington's Pharmaceutical Sciences 16th edition, Osol, A. Ed. (1980)), in the form of aqueous solutions. The cells will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The cells can be administered by any suitable means, usually parenteral. Parenteral infusions include intramuscular, intravenous (bolus or slow drip), intraarterial, intraperitoneal, intrathecal or subcutaneous administration.

Methods of Treatment

The invention further provides methods for reducing growth of cancer cells, e.g., hematologic malignancies. The methods provide for decreasing the number of cancer cells expressing CD93. In general, the methods comprise contacting a cancer cell with an anti-CD93 CAR-T cells; or an anti-CD93 antibody or fragment derived therefrom, usually contacting in vivo under conditions that cause cell death of the CD93 expressing cancer cells, e.g. by T-cell mediated cytotoxicity, ADCC, by increase of phagocytosis, etc., in a dose sufficient to reduce cancer cell growth and treat the cancer.

In an embodiment, the cancer is a hematological malignancy. In an embodiment, the hematological malignancy is a leukemia. On some embodiments the hematological malignancy is a pre-leukemia, e.g. myelodysplastic syndrome (MDS) or myeloproliferative neoplasm (MPN). In another embodiment, the hematological malignancy is a leukemia. In an embodiment, the hematological malignancy is a lymphoma. In an embodiment the hematologic malignancy is a myeloma.

In an embodiment, the leukemia is selected from acute myeloid leukemia (AML), mixed lineage leukemia (MLL), acute lymphocytic leukemia (ALL), chronic lymphocytic leukemia (CLL) and chronic myelogenous leukemia (CML), myelodysplastic syndrome (MDS), myeloproliferative neoplasms (MPNs). In an embodiment, the leukemia is AML. In an embodiment, the leukemia is MLL.

"Reducing growth of cancer cells" includes, but is not limited to, reducing proliferation of cancer cells, and reducing the numbers if viable cancer cells in a patient tissue, e.g. blood, bone marrow, lymph nodes, etc. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood or biopsy of the individual.

In some embodiments, the methods may include administering to a subject in need thereof an effective amount of T cells expressing an anti-CD93 CAR. In one embodiment, a subject having a hematologic malignancy is administered an effective amount of autologous or allogeneic T cells expressing an anti-CD93 CAR to treat the cancer. The CAR-T cell population may be engineered and expanded ex vivo. In addition to CD93, the CAR or a second CAR present in the T cell, may recognize a second antigen present on the surface of the cancer cells such that, upon binding of both the second antigen and CD93, the immune cell expressing the CAR is activated. Individual immune cells of the population may express the CAR and a second CAR, e.g. an iCAR or TAN-CAR. An immune response may be manifest as an increase in the cytolytic response of T cells towards the target cells present in the recipient, e.g. towards elimination of tumor cells; and the like.

Where the contacting is performed in vivo, an effective dose of engineered cells is infused to the recipient. Dosage and frequency may vary depending on the agent; mode of administration; nature of the cytokine; and the like. It will be understood by one of skill in the art that such guidelines will be adjusted for the individual circumstances. The dosage may also be varied for localized administration, e.g. intranasal, inhalation, etc., or for systemic administration, e.g. intramuscularly (i.m.), intraperitoneally (i.p.), intravenously (i.v.), and the like. Generally at least about $10^4$ engineered cells/kg, at least about $10^5$ engineered cells/kg; at least about $10^6$ engineered cells/kg, at least about $10^7$ engineered cells/kg, or more are administered to the recipient.

Where treatment comprises administering an anti-CD93 antibody, the antibody may be conjugated to a chemotherapeutic drug that reduces cancer cell growth. Thus, in some embodiments, the invention provides a method of delivering a drug to a cancer cell, comprising administering a drug-antibody complex to a subject, wherein the antibody is specific for CD93, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art.

Samples, including tissue sections, slides, etc. suspected of containing cancer cells, are stained with reagents specific for CD93, e.g. an anti-CD93 ABD construct. Samples may be frozen, embedded, present in a tissue microarray, and the like. The reagents, e.g. antibodies, polynucleotide probes, etc. may be detectably labeled, or may be indirectly labeled in the staining procedure. The information thus derived is useful in prognosis and diagnosis, including susceptibility to acceleration of disease, status of a diseased state and response to changes in the environment, such as the passage of time, treatment with drugs or other modalities. In some embodiments, such staining is performed to determine if an individual has a cancer susceptible to treatment with anti-CD93 CAR-T cells.

Anti-CD93 ABD can be used in vitro and in vivo to monitor the course of CD93 disease therapy. Thus, for example, by measuring the increase or decrease in the number of cells expressing CD93, particularly cancer cells expressing CD93, it can be determined whether a particular therapeutic regimen aimed at ameliorating disease is effective.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations.

Kits

Also provided are kits for use in the methods. The subject kits may include an expression vector encoding the anti-CD93 ABD or anti-CD93 ABD construct. In some embodiments, the components are provided in a dosage form (e.g., a therapeutically effective dosage form), in liquid or solid form in any convenient packaging (e.g., stick pack, dose pack, etc.). Reagents for the selection or in vitro derivation of cells may also be provided, e.g. growth factors, differentiation agents, tissue culture reagents; and the like.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXAMPLES

Example 1

Humanized and Chimeric Anti-Human CD93 Monoclonal Antibodies and Variants Engineered into Chimeric Antigen Receptor T Cells Generation of monoclonal antibody against human CD93. Monoclonal mouse anti-human CD93 antibodies were generated by immunization of mice using CD93-Fc fusion protein. Hybridomas were generated using standard protocols. Hybridomas were selected and supernatants from the resulting clones were screened by enzyme linked immunosorbent assay (ELISA) and flow cytometry. A mouse hybridoma clone, F11, was identified to produce a monoclonal antibody with specificity against human CD93. Heavy and light chain variable regions of F11 were cloned from the hybridoma using universal antibody primers. Multiple clones of each V gene product were sequenced to monitor PCR-induced errors. The nucleotide sequences of VH and VL of F11 were determined, and the deduced amino acid sequences are shown in FIGS. 1A and B, respectively.

Humanization of F11 antibody. In order to select human antibody frameworks (FRs) to be used as templates for CDR-grafting, the mouse F11 VL and VH regions were compared with those of human germline sequences. The FRs of mouse F11 VL region were found to have the highest homology with IGKV2D-29 subgroup, and the FRs of the VH region exhibited the highest homology with human IGHV1-2 subgroup. The FRs from human IGKV2D-29 and IGHV1-2 were therefore used as the bases for designing the humanized F11. Amino acid positions in the FR regions that differ between F11 and IGKV2D-29/IGHV1-2 sequences and that may have influence in antigen binding were identified through molecular modeling. Sequence alignments of mouse and humanized VH and VL are shown in FIG. 2.

Characterization of antigen binding activity of chimeric and humanized F11 antibody. Mouse and humanized F11 variable regions were constructed onto a human IgG1 scaffold to make chimeric F11-G1 (ChF11-G1) and humanized F11-G1 (Hu F11-G1), respectively. Transient transfection was carried out in 293 cells, and the resulting antibodies were purified by Protein A affinity chromatography. To assess the antigen binding activity of the antibodies, ELISA was conducted by coating with human CD93/Fc fusion protein as the bait. As shown in FIG. 3, HuF11-G1 bound CD93 strongly in a dose-dependent manner, as compared to ChF11-G1 that possesses the original mouse variable regions of F11 antibody, suggesting that HuF11-G1 retained similar antigen binding activity as compared to its parental antibody.

In order to enhance antibody Fc-dependent effector functions, a HuF11-G1 mutant (HuF11-G1 TM) that contains triple G236A/S239D/I332E mutations in the Fc constant region was constructed. G236A/S239D/I332E mutations in the constant region had no effect on the antibody binding to the antigen (FIG. 3).

Expression profile of CD93 on normal human peripheral leukocytes and human primary leukemic cells. CD93 expression was examined on normal human peripheral blood by flow cytometry using antibodies specific to different blood subsets. CD93 expression was detected on monocytes and neutrophil cells, but not on red blood cells, platelets, lymphocytes, or NK cells (FIG. 4). CD93 expression was further investigated on human primary leukemic cells. CD93 was detected on acute leukemia associated with rearrangements of the mixed lineage leukemia 1 gene (rMLL) (n=11) and acute myeloid leukemia (AML) cells (n=14) (FIG. 5).

Figure 6:
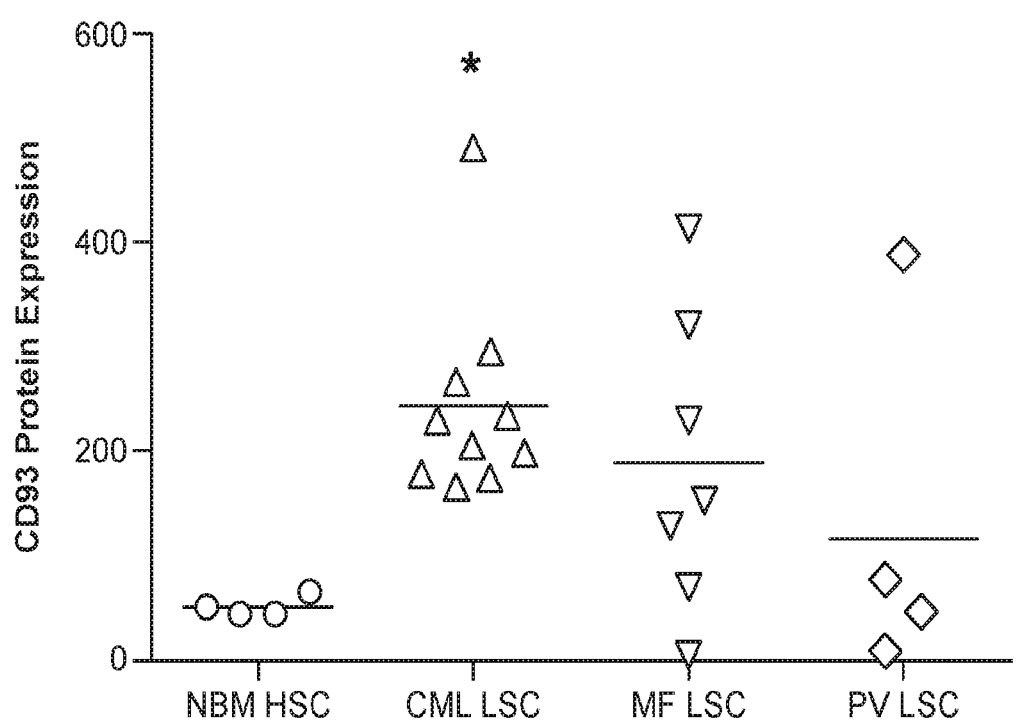
FIG. 6. CD93 expression on normal human hematopoietic stem cells and leukemic stem cells from various myeloproliferative neoplasms including chronic myeloid leukemia (CML), myelofibrosis (MF), and polycythemia vera (PV).

Moreover, CD93 expression was tested on multiple samples of normal bone marrow (NBM) hematopoietic stem cells (HSC), and primary chronic myeloid leukemia (CML) stem cells (LSC), myelofibrosis (MF) LSC, and polycythemia vera (PV) LSC. CD93 is expressed on CML LSC, and a subset of MF and PV LSC—but not on all normal HSC (FIG. 6). These results show that CD93 is a marker of MPN LSC and has therapeutic potential.

Generation of chimeric antigen receptor T cells based on the scFv sequence of CD93 antibody huF11. In order to generate chimeric antigen receptor (CAR) T cells using the CD93 scFv with either CD28 or 41-BB co-stimulation domains, four constructs were created and cloned into the retroviral vector MSGV1. These constructs were transfected to create retrovirus, which was then transduced into primary human T cells to create CD93 CAR T cells using standard techniques. As demonstrated in FIG. 7, the constructs were designated F11 28ζ L-H, F11 28ζ H-L, F11 BBζ L-H, and F11 BBζ H-L. Expression of CAR T cells was detected by flow cytometry with CD93-Fc fusion protein followed by anti-human IgG Fc secondary antibody in order to quantify transduction efficiency. All CAR variants were consistently expressed at similar levels on primary T cells with a >90% transduction efficiency (FIG. 7).

Figure 8A:
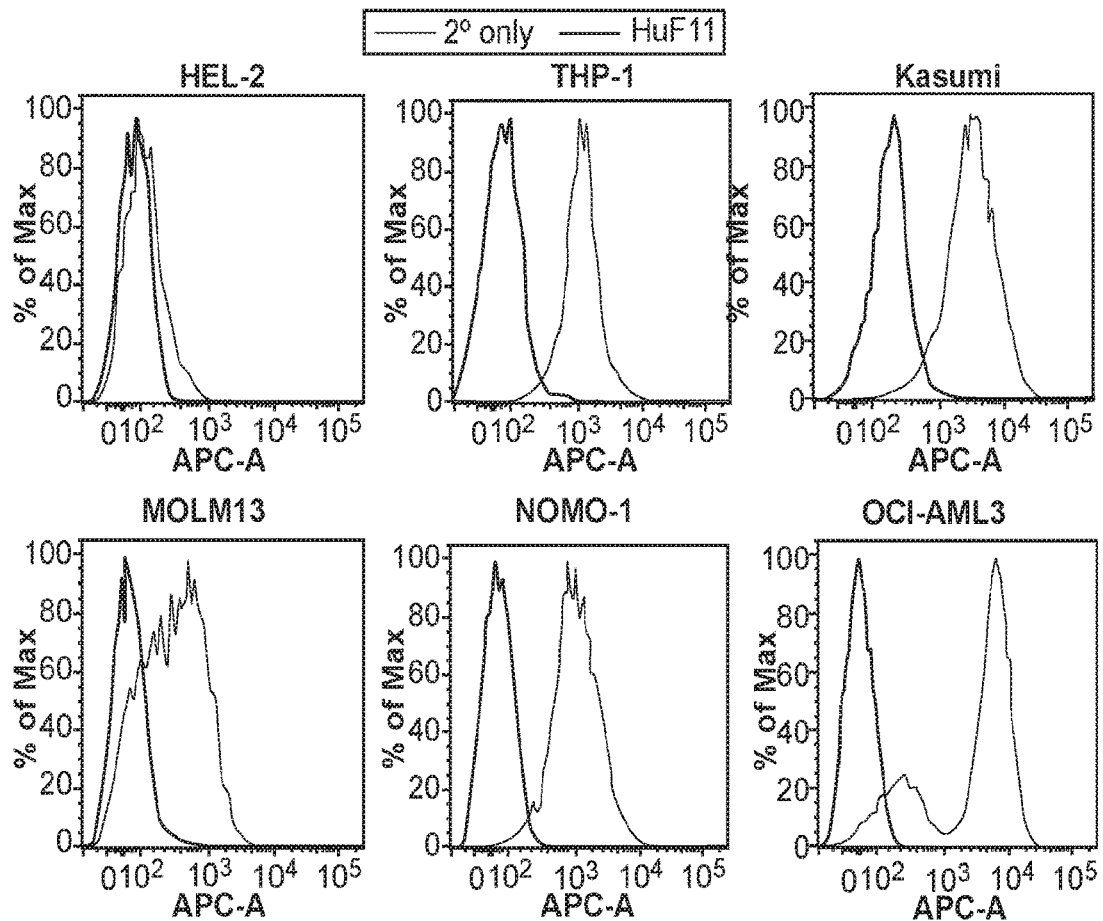
FIG. 8. CD93-specific CAR T cells produce cytokines when incubated with CD93 positive AML cell lines. A. AML cell lines were first treated with Fc block, then were stained with biotinylated HuF11 antibody followed by streptavidin APC, or with streptavidin APC only as a control. CD93 was highly expressed on many AML cell lines including THP-1, Kasumi, MOLM-13, NOMO-1, and OCI-AML3, and was not expressed on HEL-2. B. $1 \times 10^5$ AML cells were incubated with $1 \times 10^5$ mock, F11 28ζ LH, F11 28ζ H-L, F11 BBζ L-H, or F11 BBζ H-L CAR T cells for 24 h. At 24 h, supernatant was harvested and ELISA was performed for IFNγ and IL-2. Results are representative of at least three independent experiments.
Figure 8B:
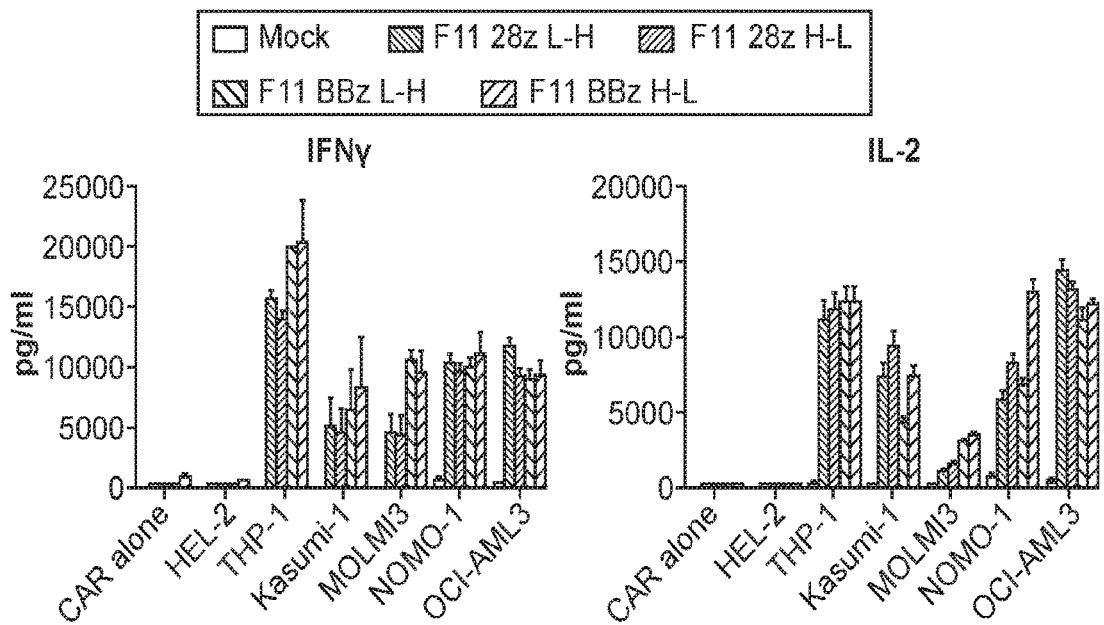

CD93-specific CAR T cells produce cytokines when incubated with CD93 positive AML cell lines. As seen in FIG. 8A, CD93 is expressed at high levels on many immortalized AML cell lines, including THP-1, Kasumi-1, MOLM13, NOMO-1, and OCI-AML3. HEL-2 cells did not have measurable CD93 expression above background so were used as a control in cytokine assays. To assess activity of the CD93 CAR T cells described above, $1 \times 10^6$ CAR T cells were co-incubated with $1 \times 10^6$ AML cells from the indicated cell lines for 24 hours followed by measurement of IFNγ and IL-2 production by ELISA. High levels of IFNγ and IL-2 were produced against all cell lines with high CD93 positivity, including THP-1, Kasumi-1, MOLM13, NOMO-1, and OCI-AML3. There was a very low level of baseline cytokine production from all CARs (CAR alone) and against a negative control AML cell line without CD93 expression (HEL-2). There were no reproducible, significant differences in the level of cytokine expression among the four CAR variants (FIG. 8B).

Figure 9:
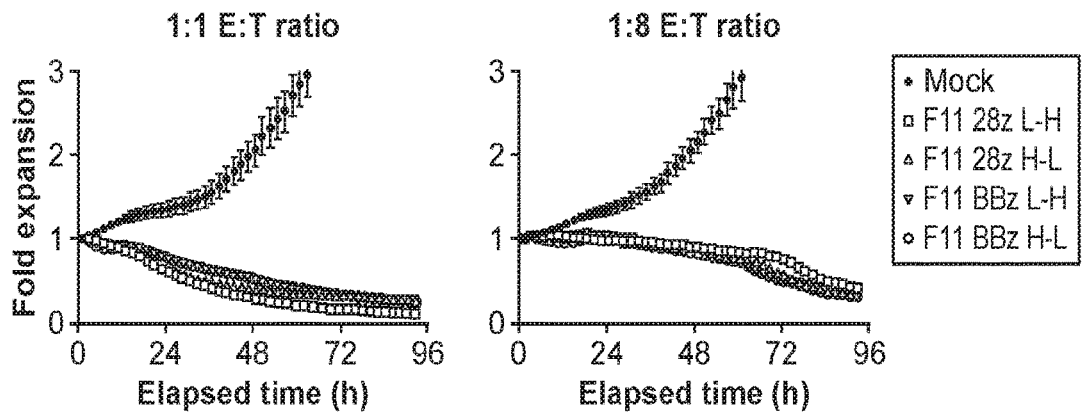
FIG. 9. CD93 CAR T cells effectively kill AML cells in vitro. $5 \times 10^4$ THP-1 AML cells stably expressing GFP were incubated with mock, F11 28ζ L-H, F11 28ζ H-L, F11 BBζ L-H, or F11 BBζ H-L CAR T cells for 96 h at E:T ratios of 1:1 (left) or 1:8 (right). An in vitro IncuCyte® killing assay measured fold change in GFP expression over time as a surrogate for cell growth. Results are representative of at least three independent experiments.

CD93-specific CAR T cells effectively kill AML cells in vitro. An in vitro killing assay was employed to evaluate CD93 CAR efficacy against an AML cell line, THP-1. In a 96 well plate, $5 \times 10^4$ THP-1 AML cells stably transduced with GFP were co-incubated with either mock or one of the four CD93 CART cell variants, at E:T ratios varying from 1:1 to 1:8. Fold change in GFP fluorescence was measured over a period of 96 hours to demonstrate target cell growth or killing. When THP-1 cells were co-incubated with mock CAR T cells, they expanded robustly, as expected. When incubated with any of the four CD93 CAR variants, the THP-1 cells were killed quickly, with very little GFP expression remaining by 48 hours, even with an E:T ratio as low as 1:8 (FIG. 9). Similar to the cytokine secretion data, there are no significant differences in the killing effects among the four different CD93 CAR T cells. Taken together with the cytokine results from FIG. 8, these in vitro results show that the CD93 CAR T cells described herein have significant cytotoxic effect against target AML cells.

Figure 10A:
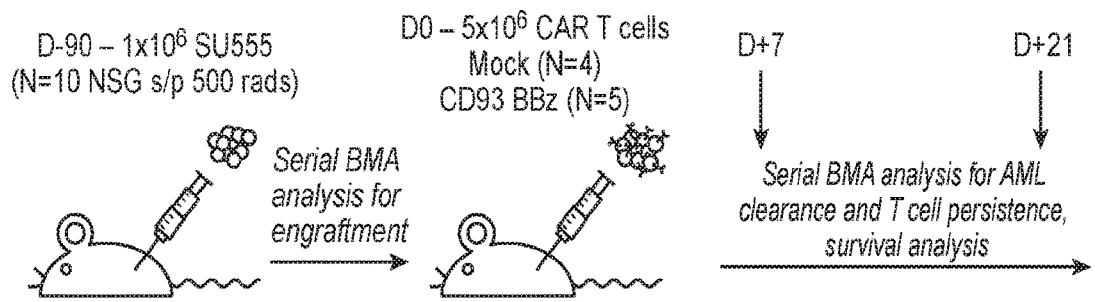
FIG. 10. CD93 CAR T cell efficacy and persistence in a patient derived xenograft model. (A) Experimental design: $1 \times 10^6$ SU555 AML cells were injected into irradiated NSG, and serial bone marrow aspirates (BMA) showed adequate levels of engraftment 3 months later. Mice were randomized and treated with $5 \times 10^6$ mock transduced (N=4) or CD93 BBz (N=5) CAR T cells, then followed with serial BMA for clearance of leukemia and persistence of T cells. (B) Leukemia engraftment (% CD45+CD33+) and (C) CAR T cell persistence (% CD45+CD3+) were measured by flow cytometry from BMA on the day of CAR T treatment and 7 and 21 days later. (D) Survival curves were generated. Differences in survival were statistically significant based on Gehan-Breslow-Wilcoxson test.
Figures 10B, 10C:
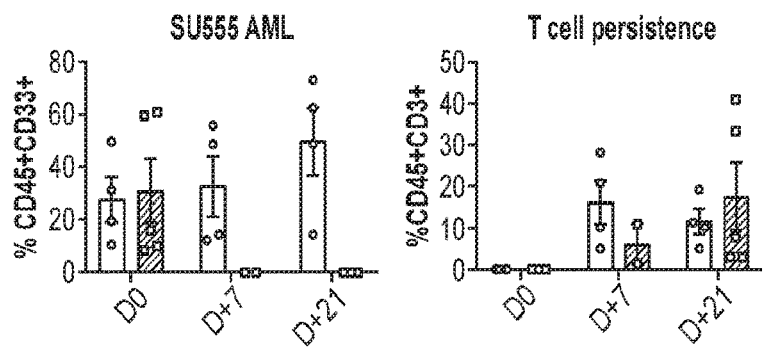
Figure 10D:
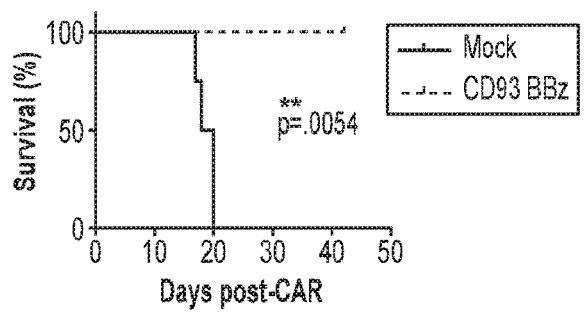
Figure 11A:
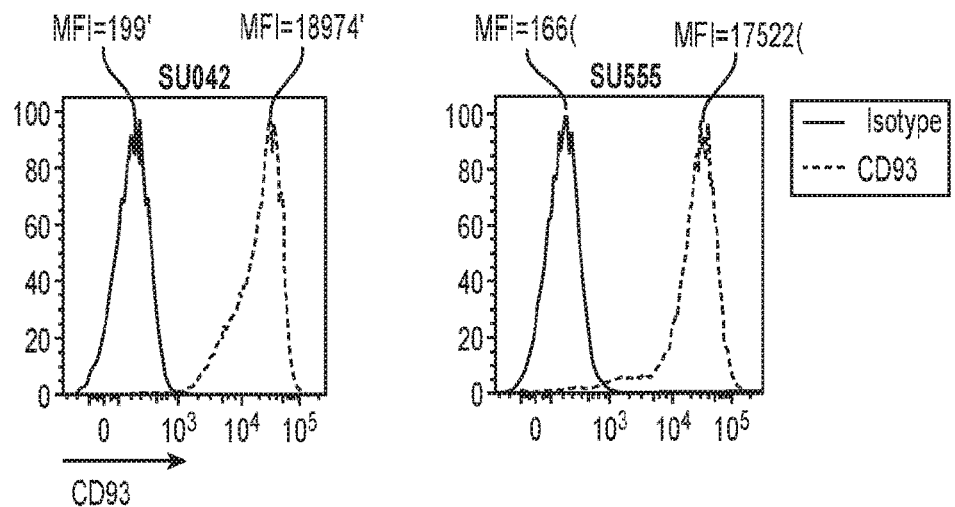
FIG. 11. CD93 expression on primary AML samples, HSCs, and AML cell lines. (A) CD93 is highly expressed on primary AML samples SU042 and SU555 as analyzed by staining with CD93 antibody compared to isotype control. (B) Fold difference in CD93 expression on primary patient AML samples, MLL-rearranged (MLLr) and non MLLr leukemias, compared to that on HSCs. (C) AML cell lines stained with the humanized mCD93 antibody (F11) show CD93 positivity on most AML cell but staining times heterogeneous among and sometimes within each cell line. (D) CD93 is expressed on monocytes and on neutrophils at low levels but not on other mature hematopoietic cells.
Figure 11B:
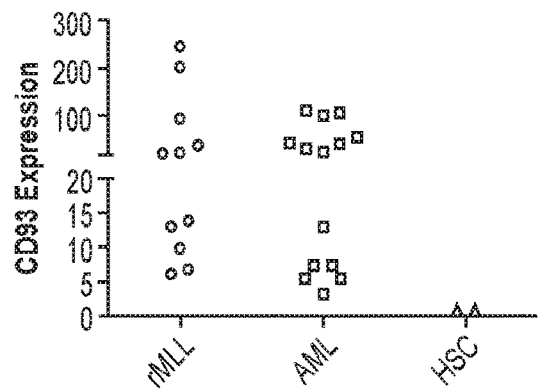
Figure 11C:
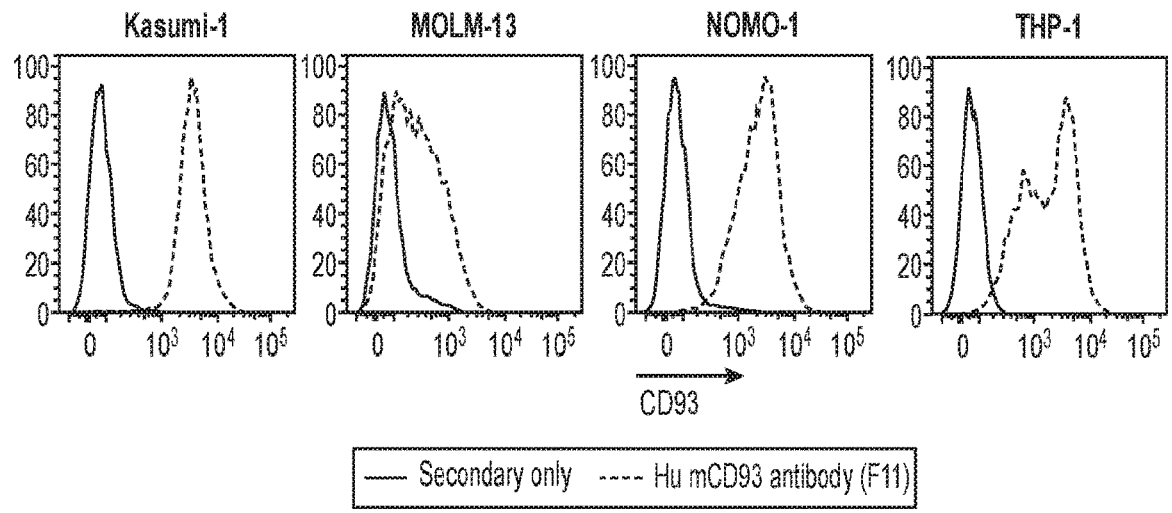
Figure 11D:
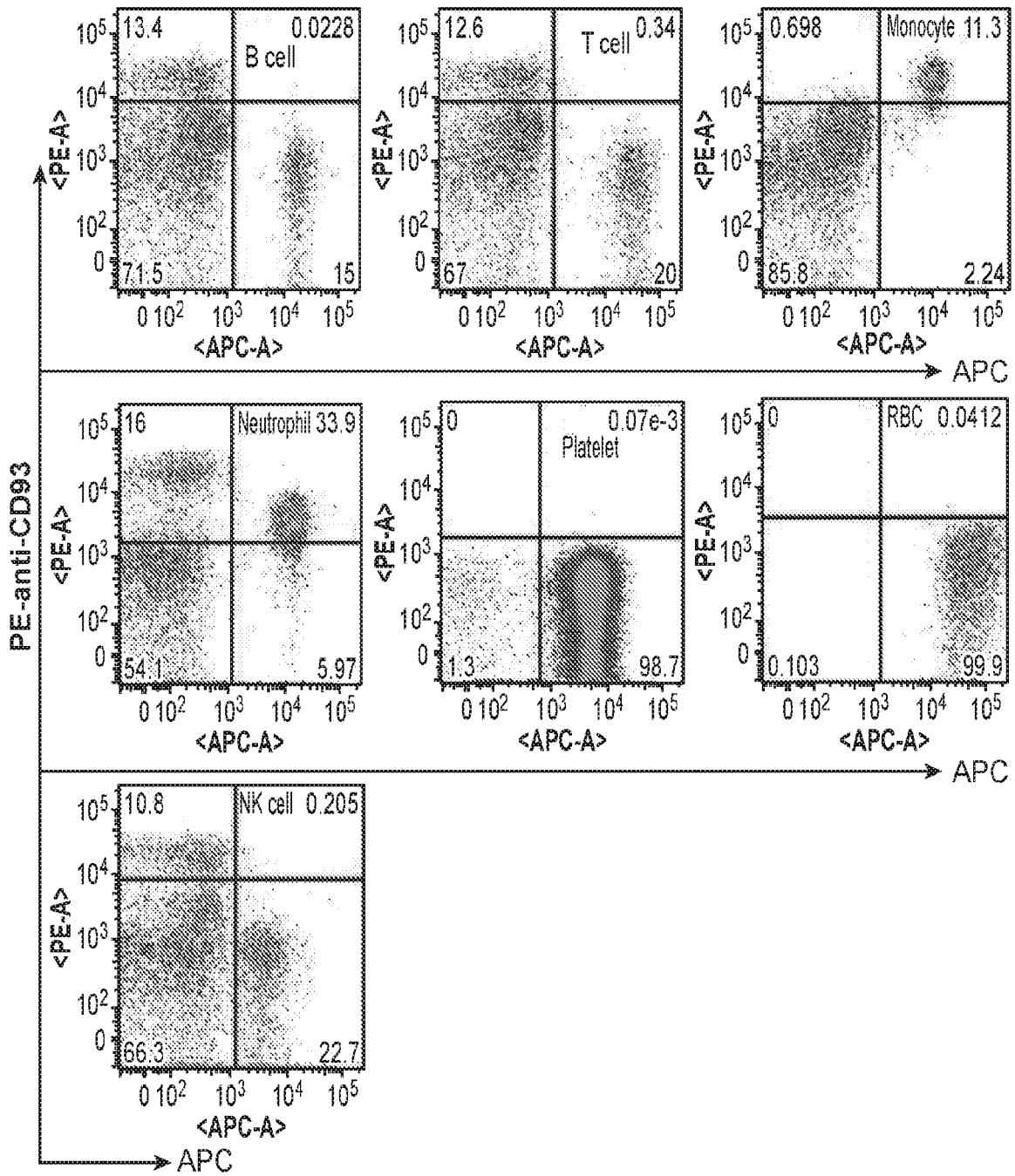
Figure 14A:
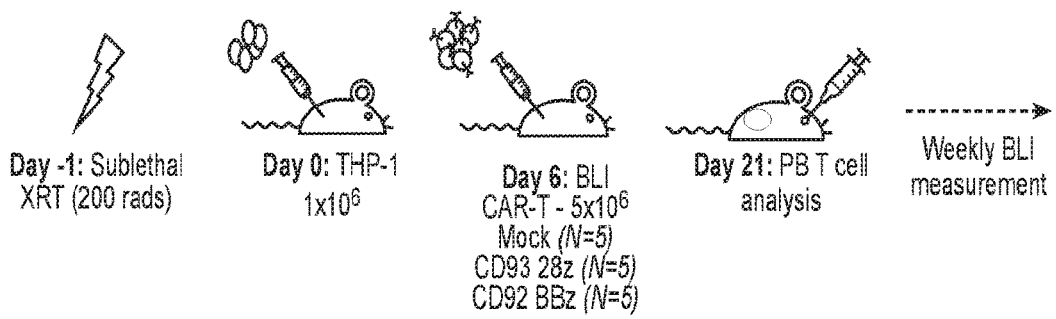
FIG. 14. CD93 CAR T cell efficacy in a THP-1 AML xenograft model. (A) Experimental design: $1 \times 10^6$ luciferase-expressing THP-1 AML cells were injected into irradiated NSG mice (N=15), and $5 \times 10^6$ mock transduced (N=5), CD93 28z (N=5), or CD93 BBz (N=5) CAR T cells were injected 6 days later after randomization. Luminescence was monitored as a surrogate for leukemic burden. (B) Photos demonstrating bioluminescence as measured by IVIS Spectrum during the 4 weeks after CAR T cell treatment. (C) Average bioluminescence demonstrates leukemic control by CD93 CAR T cells, especially with CD93 28z CAR. (D) T cell expansion was measured at day 14 post-CAR to correlate tumor response to T cell expansion.
Figure 14B:
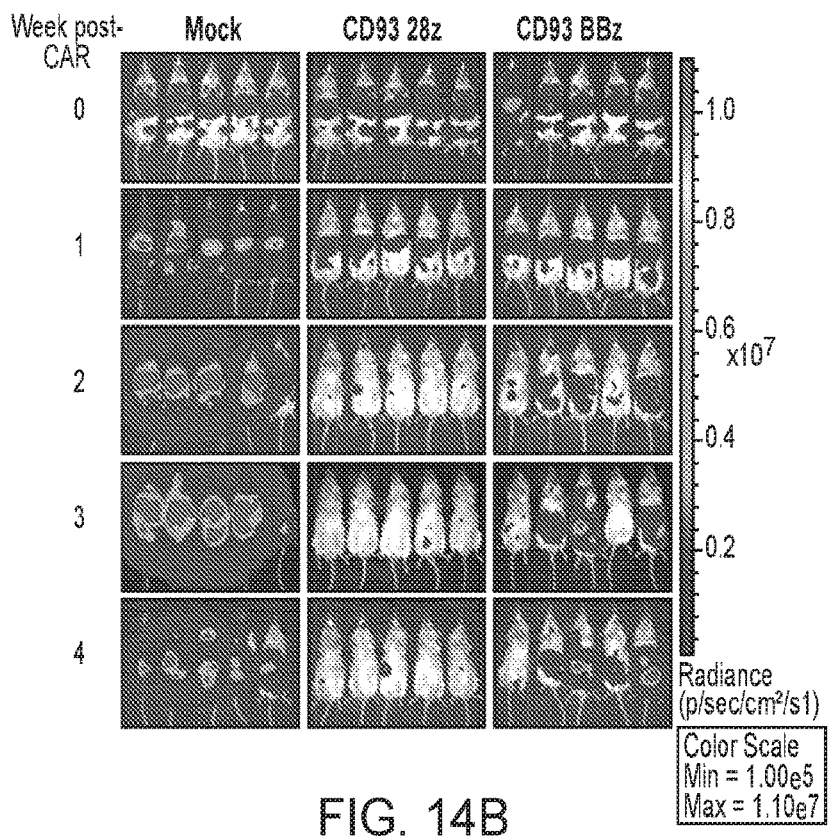
Figure 14C:
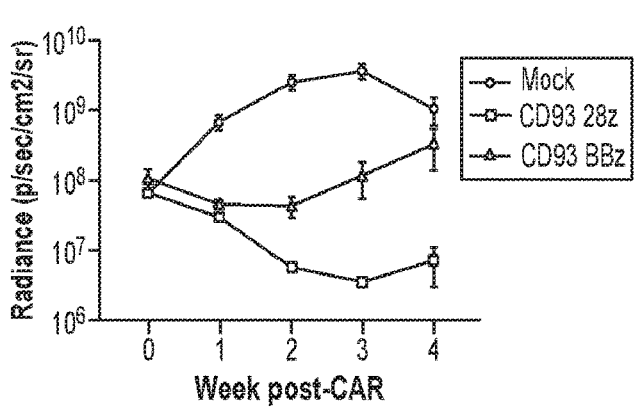
Figure 14D:
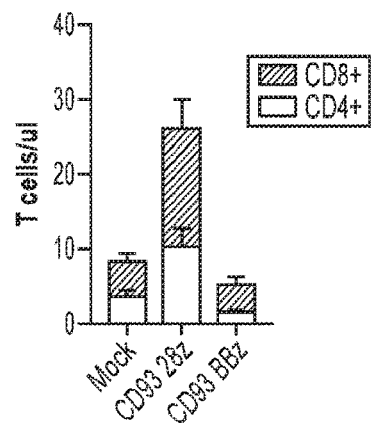
Figures 16A, 16B, 16C:
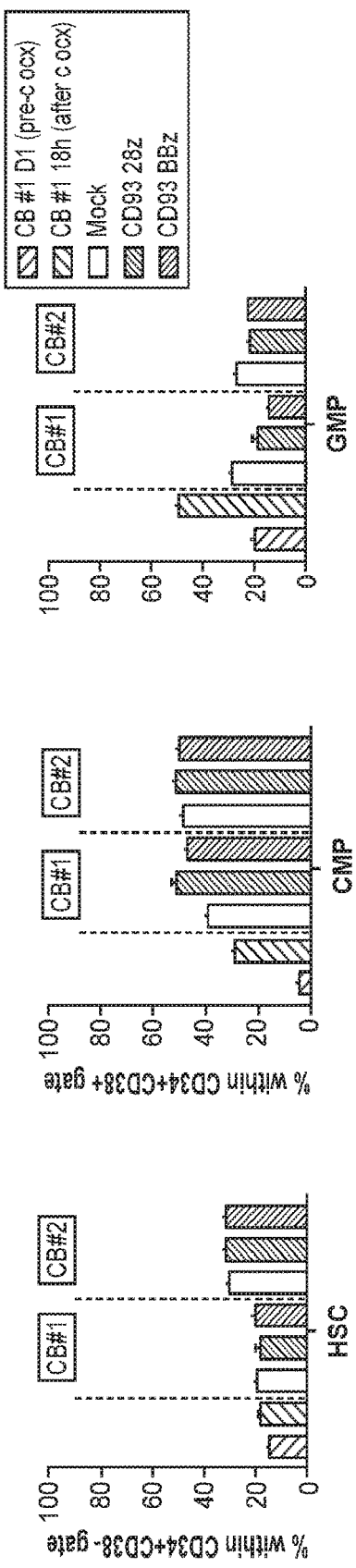
FIG. 16. CD93 CAR T cells do not target hematopoietic progenitor (HPC), either by affecting viability or colony forming ability. (A) Day 10 mock CAR T cells or CD93 CAR T cells were incubated with CD34+ cells isolated from human cord blood. After 24 h of coculture, prevalence of each progenitor population (hematopoietic stem cells, HSC; common myeloid progenitors, CMP; granulocyte monocyte progenitors, GMP) within the CD34+ cell population was measured (N=2 cord blood samples) (B) CD93 CAR T cells do not produce IFNγ after coculture with CD34+ cells derived from human cord blood. (C) Colony forming assays show no impairment of CFU-G/M/GM or CFU-E after coculture with CD93 CAR T cells.
Figure 17A:
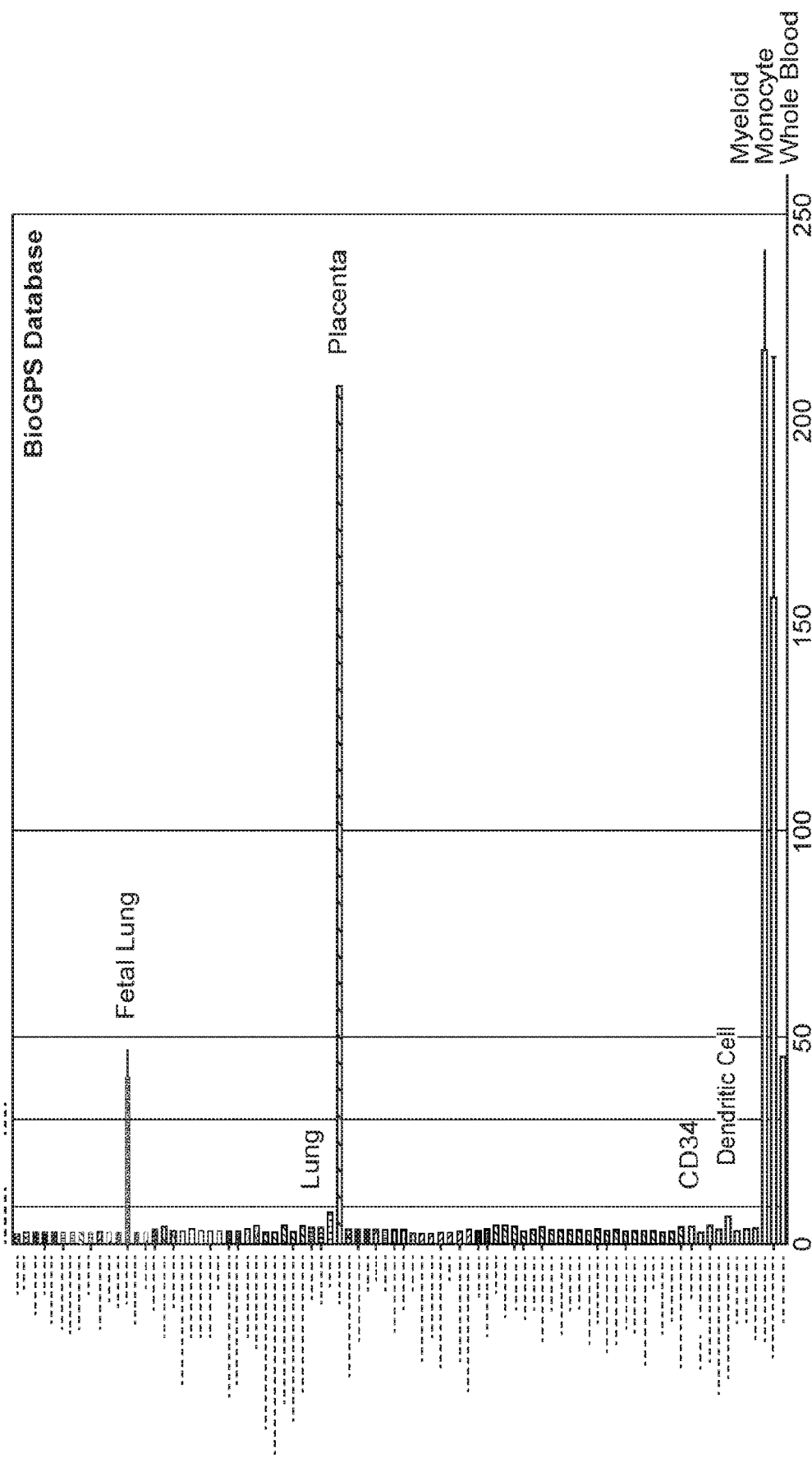
FIG. 17. CD93 has low expression on non-developmental normal tissues, but is expressed highly on endothelial cells. (A) Analysis of CD93 by RNA expression based on data derived from BioGPS Database. There is no expression or very low expression with the exception of some hematopoietic tissues and developmental tissues. (B) IHC of a normal tissue microarray demonstrates some minimal CD93 expression in pancreas, diaphragm, skeletal muscle, and lung. (C) Within multiple tissues, CD93 expression is seen by IHC on the endothelial cells. (D) Using immortalized HUVECs as a model system, CD93 expression was compared to AML cell lines and is equivalent. (E) CD93 CAR T cells produce IFNγ when cocultured with iHUVECs for 24 h.

CD93-specific CAR T cells can eliminate AML in viva The CD93 28ζ L-H CAR T cells were tested in a patient derived xenograft mouse model to assess in vivo efficacy. Nine NRG mice were irradiated and received $1 \times 10^6$ SU555 human leukemia cells, a primary AML specimen which is known to have high expression of CD93 (See FIG. 5A). Serial bone marrow aspirations were done until all mice had measurable and reproducible levels of engraftment of human leukemia, defined by percentage of CD33 positive human leukocytes within the bone marrow compartment. Engraftment levels ranged from 0.15% to 35%, and mice were divided into two groups with equivalent average engraftment levels of ~9%. Four mice were injected via tail vein with $10 \times 10^6$ mock CAR T cells and five mice were injected with $10 \times 10_6$ CD93 28ζ L-H CAR T cells. After CAR T cell injection, survival curves were generated for a period of 40 days. All mice that received CD93 CAR T cells had no detectable human AML, whereas all mock treated animals did not survive past 20 days. (FIG. 10).

Sequences. The F11 mouse heavy chain variable region protein comprises the amino acid sequence (SEQ ID NO:1) EVQLQQSGPE LVKPGASVKI PCKASGYTFT DYHMDWVKQS HGKSLEWIGD IDPYNGDTVF NQKFKGKATL TVDKSSSTAY MELRSLTSED TAVYYCTRGG DYWGQGTTLT VSS. The humanized version of the VH comprises the sequence (SEQ ID NO:2) QVQLVQSGAE VKKPGASVKV SCKASGYTFT DYHMDWVKQA PGQGLEWIGD IDPYNGDTVF NQKFKGKATM TRDTSISTAY MELSRLRSDDT AVYYCTRGGD YWGQGTLVTV SS. The VH CDR sequences were identified as follows. CDR1 (SEQ ID NO:3) DYHMD; CDR2 (SEQ ID NO:4) DIDPYNGDTVFNQKFKG; CDR3 (SEQ ID NO:5) GGDY.

The F11 mouse light chain variable region protein comprises the amino acid sequence (SEQ ID NO: 6) DVVMTQTPLS LPVSLGDQAS ISCRSSQTLV HSNGNTYLHW YLQKPGQSPK LLIYKVSNRF SGVPDRFSGS GSGTDFTLKI SRVEAEDLGV YFCSQSTHVP FTFGSGTKLE IK. The humanized version of the VL comprises the sequence (SEQ ID NO:7) DIVMTQTPLS LSVTPGQPAS ISCRSSQTLV HSNGNTYLHW YLQKPGQPPQ LLIYKVSNRF SGVPDRFSGS GSGTDFTLKI SRVEAEDVGV YFCSQSTHVP FTFGQGTKLE IK. The VL CDR sequences were identified as follows: CDR1 (SEQ ID NO:8) RSSQTLVHSNGN-TYLH; CDR2 (SEQ ID NO:9) KVSNRFS; CDR3 (SEQ ID NO:10) SQSTHVPFT.

Example 2

Five year overall survival rates for pediatric acute myeloid leukemia (AML) approach 70%, but for patients with high risk features or relapsed disease, novel therapies are desperately needed. The significant inter- and intra-patient heterogeneity in antigen expression mandates that CARs targeting specific cell surface antigens be developed. CD93 is identified as a cell surface marker prominent on leukemic blasts and expressed on leukemic stem cells, with negligible expression on HSCs and other hematopoietic progenitor cells.

CAR T cells directed against CD93 may mediate potent antileukemic activity but would not affect normal myeloid progenitor populations. CAR T cells directed against CD93 based on the scFv from a humanized murine antibody were developed in our lab. CD93 CAR T cells can be reproducibly generated to large quantities with high CAR surface expression, and do not express high levels of inhibitory receptors that are associated with T cell exhaustion. When co-incubated with CD93-positive AML cell lines, CD93 CAR T cells secrete cytokines and exhibit cytotoxicity. They do not affect HSC or hematopoietic progenitor viability or colony forming ability. In murine xenograft models of AML, CD93 CAR T cells demonstrate anti-leukemic effect in multiple models. Endothelial cells also express CD93 and are targeted by CD93 CAR T cells. Therefore, CD93 CAR T cells have the potential to contribute to expanding immunotherapy options for patients with AML but will require combinatorial engineering strategies to safely translate this as a clinical therapeutic.

The data presented in FIG. 11-17 demonstrate that CD93 is expressed at high levels on many leukemia cell lines and primary leukemia samples. CD93 is not expressed on hematopoietic progenitor cells and is expressed at low levels on non-developmental tissues with the exception of endothelial cells. CD93 CAR T cells based on the humanized murine scFv of the F11 antibody expand robustly and do not express high levels of exhaustion markers. CD93 CAR T cells secrete cytokines and exhibit cytotoxicity when co-incubated with AML cell lines in vitro. CD93 CAR T cells show activity in multiple in vivo xenograft models of AML and confer a survival benefit. Expression of CD93 on endothelial cells may benefit from combinatorial CAR engineering strategies in order to be viable for clinical translation (e.g. AND gate or NOT gate)

What is claimed is:

1. A polypeptide comprising an antigen-binding domain (ABD) specific for human CD93, comprising:
   a variable heavy (VH) domain comprising CDR1, CDR2 and CDR3 sequences in a VH framework, wherein CDR1, CDR2 and CDR3 comprise an amino acid sequence as set forth in SEQ ID NO:3, 4 or 5;
   and a variable light (VL) domain wherein the VL domain comprises CDR1, CDR2 and CDR3 sequences in a VL framework, wherein CDR1, CDR2 and CDR3 comprise an amino acid sequence set forth in SEQ ID NO:8, 9 and 10.

2. The polypeptide of claim 1, wherein the VH domain comprises a sequence of SEQ ID NO:1 or SEQ ID NO:2.

3. The polypeptide of claim 1, wherein the VL domain comprises a sequence of SEQ ID NO:6 or SEQ ID NO:7.

4. The polypeptide of claim 1, wherein the VH and VL framework sequences are human framework sequences.

5. The polypeptide of claim 1, wherein the ABD is a single chain variable polypeptide (scFv).

6. The polypeptide of claim 1, wherein the ABD is joined to a human Fc sequence.

7. The polypeptide of claim 1, wherein the polypeptide is a chimeric antigen receptor (CAR).

8. A nucleic acid encoding the polypeptide according to claim 1.

9. A nucleic acid vector comprising the nucleic acid of claim 8.

10. A mammalian cell genetically engineered ex vivo to comprise the vector of claim 9, wherein the vector encodes a polypeptide comprising an antigen-binding domain (ABD) specific for human CD93 and which cells expresses the polypeptide comprising an antigen-binding domain (ABD) specific for human CD93, wherein the cell is optionally a human cell, a stem cell, a T cell, or a CD8$^+$ T cell.

11. The cell of claim 10, wherein the cell is isolated from an individual with a hematologic malignancy or from a healthy donor.

12. A pharmaceutical formulation comprising a population of cells according to claim 10.

13. A method of treating an individual for cancer, the method comprising:
   administering to an individual in need thereof an effective dose of population of cells according to claim 10.

14. The method of claim 13, wherein the cancer is a hematologic malignancy.

15. The method of claim 14, wherein the hematologic malignancy is a myeloma.

16. The method of claim 14, wherein the hematologic malignancy is a lymphoma.

17. The method of claim 14, wherein the hematologic malignancy is a leukemia.

18. The method of claim 17, wherein the leukemia is acute myeloid leukemia.

19. The method of claim 17, wherein the leukemia is mixed lineage leukemia.

20. The method of claim 14, wherein the hematologic malignancy is a myelodysplastic syndrome neoplasm (MDS) or a myeloproliferative neoplasm (MPN).

* * * * *

SEQUENCE LISTING

```
<160> NUMBER OF SEQ ID NOS: 10

<210> SEQ ID NO 1
<211> LENGTH: 113
<212> TYPE: PRT
<213> ORGANISM: Artificial sequence
<220> FEATURE:
<223> OTHER INFORMATION: synthetic sequence

<400> SEQUENCE: 1

Glu Val Gln Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

His Met Asp Trp Val Lys Gln Ser His Gly Lys Ser Leu Glu Trp Ile
        35                  40                  45

Gly Asp Ile Asp Pro Tyr Asn Gly Asp Thr Val Phe Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Thr Arg Gly Gly Asp Tyr Trp Gly Gln Gly Thr Thr Leu Thr Val Ser
            100                 105                 110

Ser

<210> SEQ ID NO 2
<211> LENGTH: 113
<212> TYPE: PRT
<213> ORGANISM: Artificial sequence
<220> FEATURE:
<223> OTHER INFORMATION: synthetic sequence

<400> SEQUENCE: 2

Gln Val Gln Leu Val Gln Ser Gly Ala Glu Val Lys Lys Pro Gly Ala
```

```
                1               5                   10                  15
            Ser Val Lys Val Ser Cys Lys Ala Ser Gly Tyr Thr Phe Thr Asp Tyr
                            20                  25                  30

His Met Asp Trp Val Lys Gln Ala Pro Gly Gln Gly Leu Glu Trp Ile
                            35                  40                  45

Gly Asp Ile Asp Pro Tyr Asn Gly Asp Thr Val Phe Asn Gln Lys Phe
                        50                  55                  60

Lys Gly Lys Ala Thr Met Thr Arg Asp Thr Ser Ile Ser Thr Ala Tyr
            65                  70                  75                  80

Met Glu Leu Ser Arg Leu Arg Ser Asp Asp Thr Ala Val Tyr Tyr Cys
                            85                  90                  95

Thr Arg Gly Gly Asp Tyr Trp Gly Gln Gly Thr Leu Val Thr Val Ser
                            100                 105                 110

Ser

<210> SEQ ID NO 3
<211> LENGTH: 5
<212> TYPE: PRT
<213> ORGANISM: Artificial sequence
<220> FEATURE:
<223> OTHER INFORMATION: synthetic sequence

<400> SEQUENCE: 3

Asp Tyr His Met Asp
1               5

<210> SEQ ID NO 4
<211> LENGTH: 17
<212> TYPE: PRT
<213> ORGANISM: Artificial sequence
<220> FEATURE:
<223> OTHER INFORMATION: synthetic sequence

<400> SEQUENCE: 4

Asp Ile Asp Pro Tyr Asn Gly Asp Thr Val Phe Asn Gln Lys Phe Lys
1               5                   10                  15

Gly

<210> SEQ ID NO 5
<211> LENGTH: 4
<212> TYPE: PRT
<213> ORGANISM: Artificial sequence
<220> FEATURE:
<223> OTHER INFORMATION: synthetic sequence

<400> SEQUENCE: 5

Gly Gly Asp Tyr
1

<210> SEQ ID NO 6
<211> LENGTH: 112
<212> TYPE: PRT
<213> ORGANISM: Artificial sequence
<220> FEATURE:
<223> OTHER INFORMATION: synthetic sequence

<400> SEQUENCE: 6

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Thr Leu Val His Ser
                20                  25                  30
```

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Phe Thr Phe Gly Ser Gly Thr Lys Leu Glu Ile Lys
            100                 105                 110

<210> SEQ ID NO 7
<211> LENGTH: 112
<212> TYPE: PRT
<213> ORGANISM: Artificial sequence
<220> FEATURE:
<223> OTHER INFORMATION: synthetic sequence

<400> SEQUENCE: 7

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Thr Leu Val His Ser
            20                  25                  30

Asn Gly Asn Thr Tyr Leu His Trp Tyr Leu Gln Lys Pro Gly Gln Pro
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Phe Thr Phe Gly Gln Gly Thr Lys Leu Glu Ile Lys
            100                 105                 110

<210> SEQ ID NO 8
<211> LENGTH: 16
<212> TYPE: PRT
<213> ORGANISM: Artificial sequence
<220> FEATURE:
<223> OTHER INFORMATION: synthetic sequence

<400> SEQUENCE: 8

Arg Ser Ser Gln Thr Leu Val His Ser Asn Gly Asn Thr Tyr Leu His
 1               5                  10                  15

<210> SEQ ID NO 9
<211> LENGTH: 7
<212> TYPE: PRT
<213> ORGANISM: Artificial sequence
<220> FEATURE:
<223> OTHER INFORMATION: synthetic sequence

<400> SEQUENCE: 9

Lys Val Ser Asn Arg Phe Ser
 1               5

<210> SEQ ID NO 10
<211> LENGTH: 9
<212> TYPE: PRT
<213> ORGANISM: Artificial sequence
<220> FEATURE:
<223> OTHER INFORMATION: synthetic sequence

```
<400> SEQUENCE: 10

Ser Gln Ser Thr His Val Pro Phe Thr
1               5
```